United States Patent [19]
Kanomi et al.

[11] Patent Number: 5,762,492
[45] Date of Patent: Jun. 9, 1998

[54] ORTHODONTIC APPLIANCE

[75] Inventors: Ryuzo Kanomi, Himeji; Katsuyuki Nakagawa, Otawara, both of Japan

[73] Assignee: Sankin Kogyo Kabushiki Kaisha, Osaka, Japan

[21] Appl. No.: 563,972

[22] Filed: Nov. 29, 1995

[30] Foreign Application Priority Data

| Nov. 29, 1994 | [JP] | Japan | 6-295371 |
|---|---|---|---|
| Nov. 29, 1994 | [JP] | Japan | 6-295372 |
| Nov. 29, 1994 | [JP] | Japan | 6-295373 |
| Nov. 29, 1994 | [JP] | Japan | 6-295374 |

[51] Int. Cl.$^6$ ............................................. A61C 3/00
[52] U.S. Cl. ....................................... 433/14; 433/8
[58] Field of Search ............................ 433/14 OR, 8, 433/11, 10, 13

[56] References Cited

U.S. PATENT DOCUMENTS

| 1,467,789 | 9/1923 | Griffin | 433/14 |
|---|---|---|---|
| 3,435,527 | 4/1969 | Kesling | 433/14 |
| 3,486,231 | 12/1969 | Nelson | 433/14 |
| 3,975,824 | 8/1976 | Lee | 433/14 |
| 4,527,975 | 7/1985 | Ghafari et al. | 433/8 |
| 4,687,441 | 8/1987 | Klepacki | 433/8 |
| 5,160,260 | 11/1992 | Chang | 433/8 |
| 5,470,228 | 11/1995 | Franseen et al. | 433/8 |

FOREIGN PATENT DOCUMENTS

| 0 623 320 | 11/1994 | European Pat. Off. |
|---|---|---|
| 49-56492 | 5/1974 | Japan. |
| 50-80694 | 6/1975 | Japan. |
| 56-112238 | 9/1981 | Japan. |
| 2-53057 | 11/1990 | Japan. |
| 3-12147 | 1/1991 | Japan. |
| 3-146052 | 6/1991 | Japan. |
| 3-168142 | 7/1991 | Japan. |
| 4-61855 | 2/1992 | Japan. |
| 4-227251 | 8/1992 | Japan. |
| 4-227252 | 8/1992 | Japan. |

*Primary Examiner*—John J. Wilson
*Attorney, Agent, or Firm*—Oblon, Spivak, McClelland, Maier & Neustadt, P.C.

[57] ABSTRACT

An orthodontic appliance includes a configuration which makes it difficult for dental plaque to be deposited thereon and which prevents lateral movement of an arch wire as well as precisely preforming a torque shift without an auxiliary attachment wire. The orthodontic appliance is used in dental treatment includes a bracket having an arch wire passage formed therein to extend substantially horizontally and a lock pin insertion passage for insertion of a lock pin therethrough, the lock pin being substantially vertically oriented between the surface of a tooth and the arch wire passage for pressing the arch wire toward a side further from the tooth surface to thereby position the arch wire. The lock pin insertion passage has a bow-shape jetting toward the tooth surface and the lock pin is bow-shaped such that the following mathematical expression is satisfied:

$$R_P \leq R_L$$

wherein $R_P$ is a radius of curvature of the lock pin insertion passage and $R_L$ is a radius of curvature of the lock pin such that the inner surface of the bow-shape portion of the lock pin presses the arch wire.

11 Claims, 22 Drawing Sheets

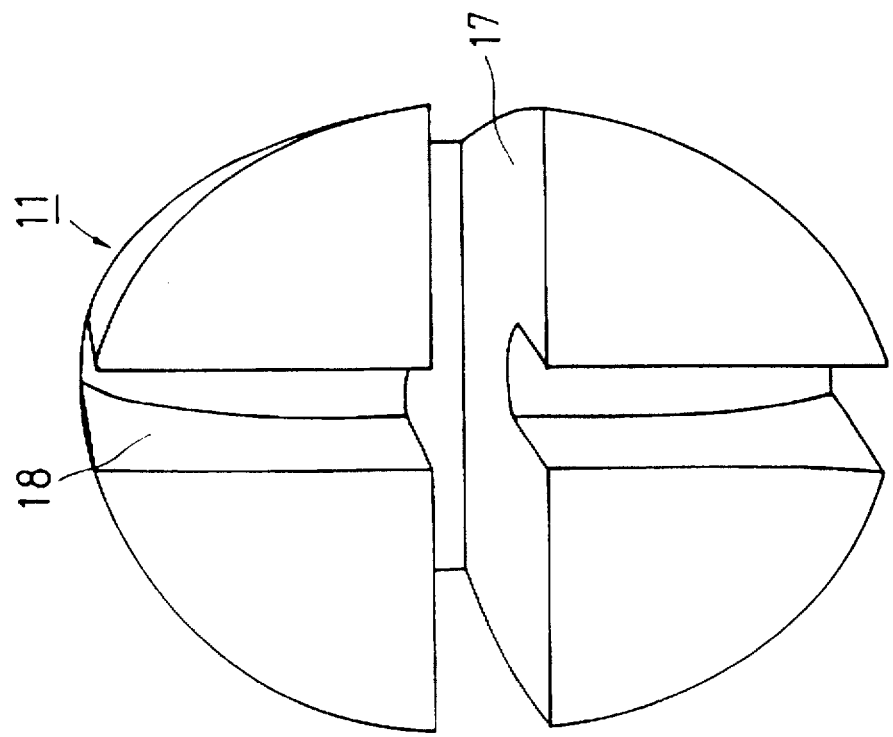
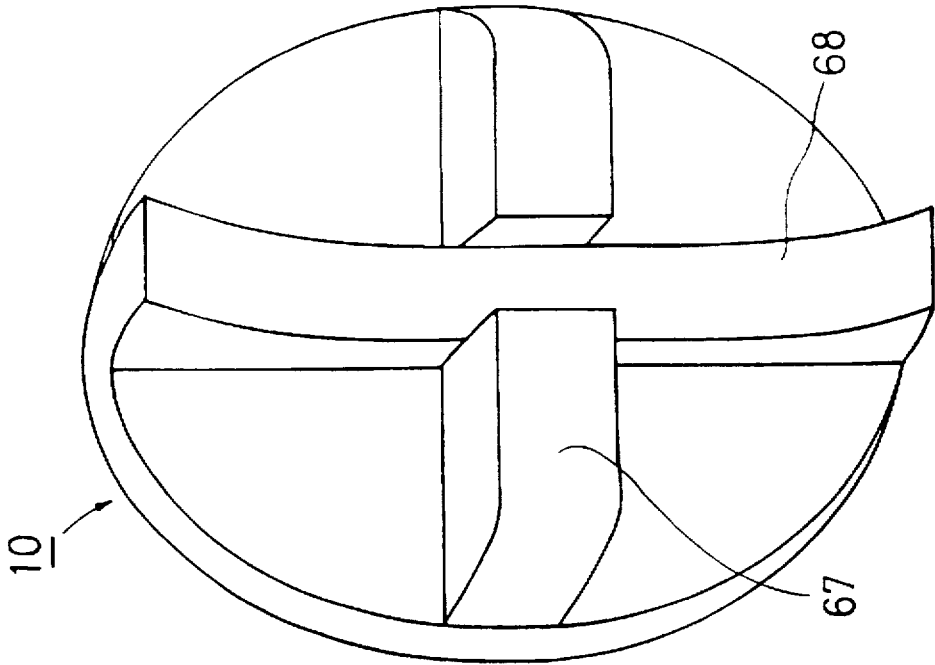

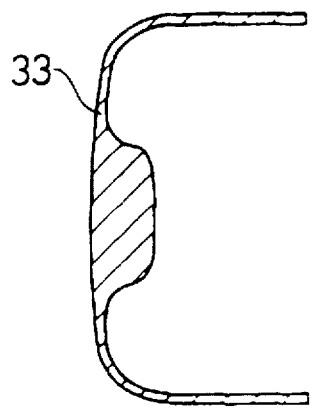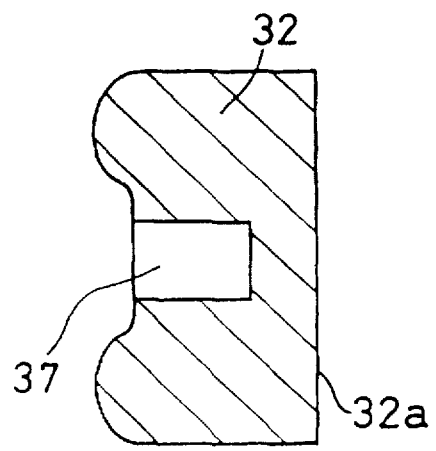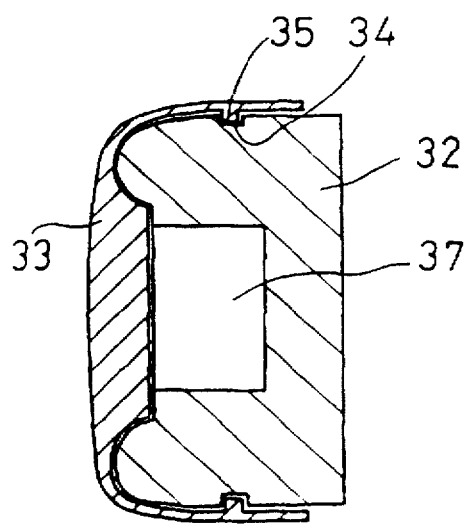

ORTHODONTIC APPLIANCE

BACKGROUND OF THE INVENTION

1. Field of the Invention

The present invention relates to an orthodontic appliance for use in dental treatment.

2. Description of the Related Art

Irregularly located teeth such as including an oblique tooth and a double tooth is disadvantageous in not only impairing an impression to look at, but also causing dental plaque to be easily deposited between the teeth in the irregular line, which results in decayed teeth and pyorrhea. For these reasons, orthodontics for patients having irregularly located teeth has recently popularized in the field of orthodontic treatment.

Orthodontic treatment is performed by a process of fixing orthodontic appliances to respective surfaces of teeth using an adhesive or the like, and threading a single arch wire through all the brackets of the orthodontic appliances at each of upper and lower jaws, so that the restoration force of the arch wire produces external forces tending to press, pull and twist the teeth. With these external forces, the teeth are placed to their correct positions and orientations in gradual treatments.

FIG. 20(a) is a perspective view showing a state where an arch wire 2 is attached to an orthodontic appliance which comprises a bracket 52 and an attachment wire 56. FIGS. 20(b) and 20(c) are each a sectional view taken along the line b—b in FIG. 20(a). The bracket 52 is adhered at its adhering surface 52a to the surface of a tooth (not shown) by an adhesive. The arch wire 2 is fitted to a fixing seat 52b provided on the bracket 52, and the bracket 52 is wound up with the attachment wire 56 as indicated by 56c in an attachment wire groove 52c so that the arch wire 2 is fixed to the bracket 52 under pressure. Hereinafter, the above orthodontic appliance will be referred to as prior art (1).

Orthodontic treatment procedures begin with primary treatment of roughly straightening the line of irregularly located teeth including oblique teeth (hereinafter referred to as a rough straightening stage). In this stage, the arch wire is not so tight fixed to the orthodontic appliances with some play left therebetween. If such a play does not exist, excessive pressing forces would be imposed on the teeth, not only making the patient feel uncomfortable, but also possibly resulting in local strengthening, which is not desired from the viewpoint of moving all the teeth to their correct positions.

Therefore, the arch wire 2 used in the rough straightening stage is generally circular in cross-section, and the arch wire 2 is fixed to the fixing seat 52b of the bracket 52 in a moderately secured condition with some play left therebetween, as explained below. More specifically, as shown in FIG. 20(b), the round arch wire 2 contacts walls of the fixing seat 52b in the form of a rectangular groove at points and, since the arch wire 2 is circular in cross-section, those contact points can easily be changed by the rolling of the arch wire 2. Accordingly, the arch wire 2 is not fixed to the fixing seat 52b so tightly. Also, in the rough straightening stage, the treatment is performed by tying up the attachment wire 56 moderately. Thus, the strength of fixation of the arch wire to the bracket is weak as a whole.

The roughly straightened teeth aligned in such a way are then finely straightened in a next treatment stage (hereinafter referred to as a right position correcting stage). In this stage, the arch wire 2 used is square in cross-section, and the attachment wire 56 is strongly tied up so that the arch wire 2 is tightly pressed against and fixed to the bracket 52. As shown in FIG. 20(c), since the square wire 2 is square in cross-section, it flatly contacts the plane walls of the fixing seat 52b in the form of a rectangular groove, and hence will not roll in the groove. Accordingly, the torque corresponding to the designed torque angle θ can continue to be applied to the tooth as designed, and the distortion of the tooth in the back and forth direction can be corrected to the right angle.

In addition to the above prior art (1), there have been proposed various types of orthodontic appliances. For example, another orthodontic appliance (2) described in Japanese Patent Laid-Open No. HEI4-61855 comprises a bracket 53 and a lock pin 54, as shown in a front view of FIG. 21, with an arch wire 2 fixed to the bracket 53 for straightening the line of teeth. The arch wire 2 is fixed in place by fitting the arch wire 2 from above to a deep arch wire groove 57 provided in the bracket 53 so as to extend horizontally, and inserting the lock pin 54 to a lock pin groove 58 in such a manner as to prevent the arch wire 2 from slipping off. The lock pin 54 is also prevented from slipping off by its lower end 54a bent.

Still another orthodontic appliance (3) described in Japanese Patent Publication No. HEI 2-53057 is arranged such that, as shown in a perspective view of FIG. 22(a) and a side view (partly sectioned) of FIG. 22(b), an arch wire 2 is laid in an arch wire groove 51 of a bracket 50 and a lock pin 55 is fitted to the arch wire groove 51. The fitted lock pin 55 is secured by bending its lower end 55a and a lock pin head 55b presses against the arch wire 2. FIG. 22(c) is a front view of the head 55b of the lock pin 55 and thereabout.

Still another orthodontic appliance(4) comprising a bracket body and a cover member is described in Japanese Patent Laid-Open No. SHO 56-112238.

In the prior art (4), as shown in a perspective view of FIG. 23, a cover member 88 includes an elastic engaging portion 89 formed by cutting vertical slits in a peripheral bent lug. A bracket body 87 includes a wire fitting groove 80 and a locking portion 81. An arch wire 2 is laid in the wire fitting groove, 80 and held in place by fitting the cover member 88 from above. When the cover member 88 is fitted to the bracket body 87, it is pressed such that the lugs of the elastic engaging portion 89 are pushed and fastened toward the center. With this pressing, the elastic engaging portion 89 is drawn toward the center to grip an outer periphery of the locking portion 81 for tight fitting. In disassembly, the center of the cover member 88 is pressed (in a direction of arrow P) to diverge the elastic engaging portion 89 outwardly, whereby the cover 88 is unlocked for removal.

In the prior art (1), however, many projections and recesses are formed on the bracket 52 and the use of the attachment wire 56 for fixing the arch wire 2 additionally increases projections and recesses. If there exist many projections and recesses on the bracket, food is liable to easily deposit in recesses, during tooth-brushing, a toothbrush has difficulties reaching the recesses. This raises the problem that dental plaque tends to deposit there and the interior of the mouth becomes unhygienic.

On the other hand, the prior art (2), (3) and (4) each have the configuration having relatively less projections and recesses and the problem of deposition of dental plaque is not so serious. However they have the problems that torque shift cannot precisely be achieved in the treatment of the right position correcting stage, and the arch wire 2 cannot be prevented from moving laterally. Here, the term "torque shift" means a treatment process of rollingly shifting the teeth toward the cheek or tongue side.

In an attempt of achieving the torque shift or preventing lateral movement of the arch wire in the orthodontic appliances of the prior arts (2) to (4), a separate auxiliary fastening means, specifically an attachment wire, is required. Using such a fastening means generates projections and recesses similarly to the prior art (1) shown in FIG. 20, which results in the problem that dental plaque tends to easily deposit and the interior of the mouth becomes unhygienic.

OBJECTS OF THE INVENTION

An object of the present invention is, therefore, to provide an orthodontic appliance which has a configuration which makes it difficult for dental plaque to be deposited thereon, and which can prevent lateral movement of an arch wire and precisely perform the torque shift without an auxiliary attachment wire even in the treatment of the right position correcting stage.

SUMMARY OF THE INVENTION

An orthodontic appliance according to a first aspect of the present invention comprising a bracket having an arch wire passage formed therein to extend substantially horizontally and a lock pin insertion passage for insertion of a lock pin there-through, and the lock pin inserted through the bracket substantially vertically between the surface of a tooth and the arch wire passage for pressing an arch wire toward the side farther from the tooth surface to thereby position the arch wire, which is charaterized in that the lock pin insertion passage has a bow-shape jutting toward the tooth surface, and said lock pin is bow-shaped with the same or a little bigger radius of the curvature as or than the Lock pin insertion passage.

The first aspect of the present invention is the same as the prior arts (2) and (3) in that the lock pin insertion passage extending substantially vertically is formed in the bracket and the lock pin is inserted through the lock pin insertion passage to hold to fix the arch wire inserted through the arch wire passage. In the first aspect of the present invention, however, the lock pin is bow-shaped and the arch wire is fixed in place such that its tooth side surface is pressed by the lock pin and the other three surfaces, i.e., upper, lower and lip/cheek side surfaces, are pressed by inner surfaces of the arch wire passage. Specifically, the above three surfaces (the upper, lower and lip/cheek side surfaces) of the arch wire are surrounded by the wall surfaces of an arch wire accommodating groove defined as the arch wire passage, and do not deviate. For the tooth side surface, even if the lock pin is vertically moved to some extent, the pressing force exerted from an inner surface of the bow-shaped lock pin will not be changed to prevent deviations of the arch wire. Therefore, even if external forces are applied to the arch wire during repeated chewing, etc., the arch wire can tightly be fixed from the four surfaces at all times. As a result, the torque shift can be achieved as designed.

Further, since the lock pin is bow-shaped, it can press the arch wire, which is polygonal (e.g., rectangular) in cross-section, on the tooth side thereof not in surface-to-surface relation but at two corners or edges of the arch wire. The arch wire can thereby be pressed more tightly. To match with the bow-shaped lock pin, the lock pin insertion passage has a bow-shape having the same or a little smaller radius of the curvature as the lock pin. If the lock pin insertion passage is designed with a little smaller radius of the curvature than the lock pin, a tip end of the lock pin is guided by the bow-shaped wall surface of the lock pin insertion passage on the outer or tooth side when the lock pin is inserted. Accordingly, the tip end of the lock pin will not be caught by the corner of the arch wire and hence the lock pin will not suffer from any blockage during its insertion, allowing the dentist to smoothly perform the treatment.

With the orthodontic appliance according to the first aspect of the present invention, the relatively smooth configuration having less projections and recesses on its surface is provided and, in addition, various degrees of strength of fixing the arch wire from moderate to tight fixing can be realized by properly selecting the thickness of the lock pin and the thickness and shape of the arch wire. Accordingly, the orthodontic appliance of the first aspect can be adapted to all the treatment stages from the rough straightening stage to the right position correcting stage. Furthermore, dental plaque is hard to deposit on the appliance and, during tooth-brushing, a toothbrush can easily reach every corner of the appliance for easier cleaning.

Preferably, the bracket comprises a tooth side member and a lip/cheek side member which are joined together undetachably. More preferably, the lip/cheek side member includes an arch wire accommodation groove extending substantially horizontally, and a lock pin insertion groove being shallower than the arch wire accommodation groove and to extend vertically while curving in a bow-shape, the tooth side member includes a horizontal ridge extending substantially horizontally in match with the arch wire accommodation groove and having such a projection height as not completely filling the arch wire accommodation groove, and a vertical ridge extending substantially vertically in match with the lock pin insertion groove and projecting in a smaller height than the horizontal ridge, and the tooth side member and the lip/cheek side member are fitted to each other under pressing into a unitary structure.

In another preferable form of the orthodontic appliance, the arch wire passage is in the form of a hooked groove with one end on the lip/ or cheek side left open, the groove being bent at its bottom into a U-shape in vertical section and extended back toward the lip/cheek side without open so as to form an arch wire seated portion.

With this preferable form, the arch wire can be fitted from the front of the patient. Further, as the above-mentioned orthodontic appliance, the appliance of this form is arranged such that the arch wire accommodated in the seated portion of the arch wire passage is held and fixed by inserting the lock pin through the lock pin insertion passage, and that the arch wire is fixed by three wall surfaces, i.e., upper, lower and one of the sides (lip/cheek side) surfaces, of the seated portion and the other surface (tooth side surface) of the arch wire is fixed by the lock pin. The above fixing of the arch wire from the three surfaces prevents deviations of the arch wire because it is surrounded by the respective wall surfaces of the seated portion. For the fixing of the arch wire from the other surface, even if the lock pin is vertically moved to some extent, the pressing force exerted from lock pin will not be changed to prevent deviations of the arch wire. Therefore, even if external forces are applied to the arch wire during repeated chewing, etc., the arch wire can tightly be fixed from the four surfaces at all times. As a result, the torque shift can be achieved as designed.

An orthodontic appliance according to a second aspect of the present invention is an orthodontic appliance wherein a bracket having an arch wire passage is comprised of a bracket body fixed to the surface of a tooth and a bracket cover for covering the bracket body in a detachable manner, which is characterized by the fact that said bracket cover is made of an elastic material, the bracket cover and the bracket body are both elliptic seen from the front side, one of the major axis and the minor axis of said elblitical bracket cover is longer than one of the major axis and the minor axis of said bracket body, and the other of the major axis and the minor axis of said bracket cover is shorter than the other of the major axis and the minor axis of said bracket body.

An orthodontic appliance according to a third aspect of the present invention comprises a bracket body fixed to the surface of a tooth and a bracket cover for covering said bracket body in a detachable manner, wherein the bracket cover is made of an elastic material, one of the bracket cover and the bracket body is circular and the other is elliptic, and the major axis of the elliptic bracket cover is longer than the diameter of the circular bracket body and the minor axis of the elliptic bracket cover is shorter than the diameter of the circular bracket body, or the diameter of the circular bracket cover is shorter than the major axis of the elliptic bracket body and is longer than the minor axis of the elliptic bracket body.

Orthodontic appliances according to second and third aspects of the present invention respectively comprise a bracket body and a bracket cover. The bracket cover is attached to and detached from the bracket body by utilizing elastic deformation property of the bracket cover. Specifically, the bracket cover is elastically deformed into such a shape as to be capable of loosely fitting to the bracket body. Upon the elastic deformation being released in the loosely fitted state, the bracket cover tends to restore its configuration before the deformation and grasps the bracket body fixedly with sandwiching press. To realize this sandwiching press, the bracket body and the bracket cover must be not similar to each other in their original states. As conditions to meet such a requirement, the aforesaid dimensional relationship between the major axis and the minor axis or these axes and the diameter are set.

With the orthodontic appliances according to the second and third aspects of the present invention, the arch wire can be fitted from the front of the tooth while ensuring a relatively smooth configuration having less projections and recesses on its surface. In addition, various degrees of strength of fixing the arch wire from moderate to tight fixing can be realized by properly selecting the thickness and shape of the arch wire. Accordingly, the orthodontic appliances of the second and third aspects can be adapted to all the treatment stages from the rough straightening stage to the right position correcting stage. Furthermore, dental plaque is hard to deposit on the instruments and, during toothbrushing, a toothbrush can easily reach every corner of the appliances for easier cleaning.

In a preferable form of the orthodontic appliances according to the second and third aspects of the present invention, the appliance further comprises a bracket and a lock pin for positioning the arch wire in the bracket, wherein the bracket is formed with both an arch wire insertion passage and a lock pin insertion passage therein, the lock pin insertion passage has a bow-shape jutting toward the tooth surface, and said lock pin is bow-shaped with the same radius or a little bigger radius of the curvature as said lock pin insertion passage.

In this preferable form, since the arch wire is fixed by using the bow-shaped lock pin, a more positive fixing of the arch wire can be realized. Further, as with the above orthodontic appliances, various degrees of strength of fixing the arch wire from moderate to tight fixing can be realized and the appliance of this form is also adaptable to all the treatment stages. Additionally, since the appliance has a relatively smooth configuration having less projections and recesses on its surface, dental plaque is hard to deposit on the appliance.

BRIEF DESCRIPTION OF THE DRAWINGS

FIGS. 5(a) and 5(b) are perspective views showing, respectively, examples of a tooth surface side member and a lip/cheek side member of a bracket according to a second embodiment of the present invention.

FIGS. 12(a) to 12(c) are sectional views of the orthodontic appliance (bracket) according to the sixth embodiment of the present invention.

DESCRIPTION OF THE PREFERRED EMBODIMENTS

As a result of studying in detail why the torque shift cannot be achieved by the prior arts (2) and (3), it has been found that the reasons therefor reside in the following observations.

Figure 21:
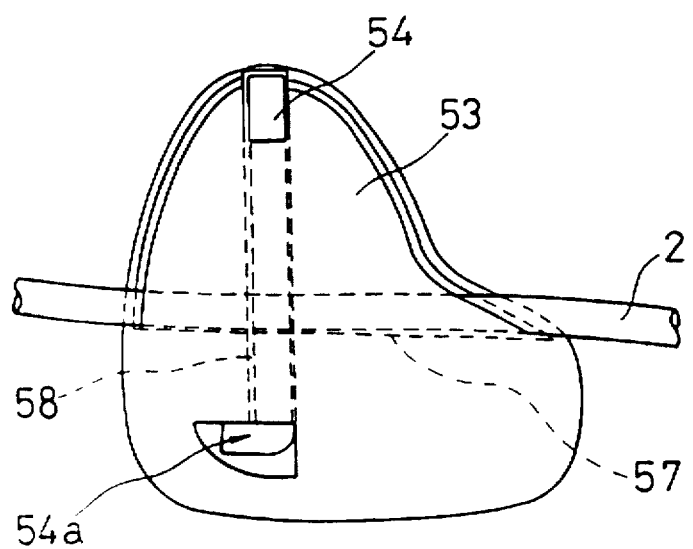
FIG. 21 is a front view of an orthodontic appliance of prior art (2).
Figure 24A:
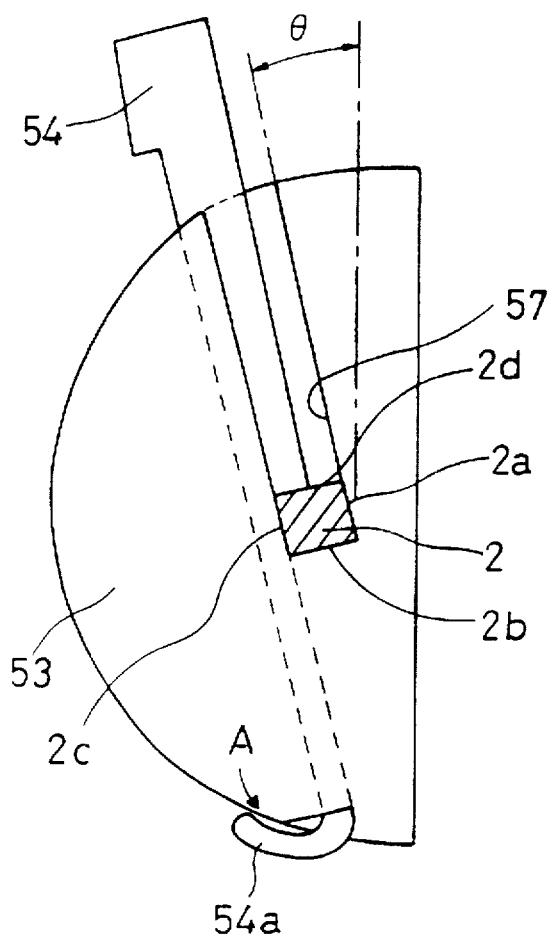
FIGS. 24(a) is a side view showing a manner in which an arch wire is fitted to the orthodontic appliance of prior art (2)
Figure 24B:
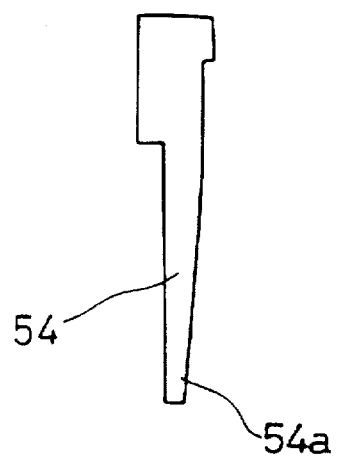
FIG. 24(b) is a side view of a lock pin in prior art (2).

FIG. 24(a) is a side view (partly including a sectional view) of the orthodontic appliance of prior art (2) (FIG. 21), the view showing a state of using a square arch wire, and FIG. 24(b) is a side view of a lock pin 54 for use in prior art (2).

In order to achieve the torque shift in the right position correcting stage, it is required to use a square arch wire 2 and to fix the arch wire 2 from four surfaces, i.e., a tooth side surface 2a, a lip/cheek side surface 2c, a bottom surface 2c and a top surface 2d, such that the wire will not be floated. By so fixing the arch wire 2 from the four surfaces, the torque shift corresponding to the designed torque angle θ can be achieved. In the orthodontic appliance of the prior art (2), however, the lock pin 54 is not correctly fixed as explained below and the top surface 2d of the arch wire 2 may not contact the lock pin 54. As a result, positive fixing of the arch wire cannot be realized.

More specifically, the lock pin 54 is locked in place by bending its lower end 54a. However it is impossible to make the inner surface of bent lower end 54a intimately close to a wall surface of the bracket 53, and a gap is inevitably caused along a bent region A. Therefore, the lock pin 54 will move vertically corresponding to the width of the gap and hence cannot hold tightly the top surface 2d of the arch wire.

The arch wire 2 can achieve the torque shift in a stable manner only when it is tightly held at all the four surfaces. If the lock pin 54 is floated as mentioned above, the position of the arch wire 2 is changed and the torque can not be applied correctly. Further, since the amount by which the lock pin 54 is floated varies depending on how the lower end 54a of the lock pin is bent in the treatment, it is practically impossible to apply the correct torque taking into consideration of the float amount of the lock pin.

As to the above-mentioned problem of lateral movement of the arch wire, it is also impossible to prevent the lateral movement of the arch wire 2 because the arch wire 2 cannot sufficiently be held.

Figure 22B:
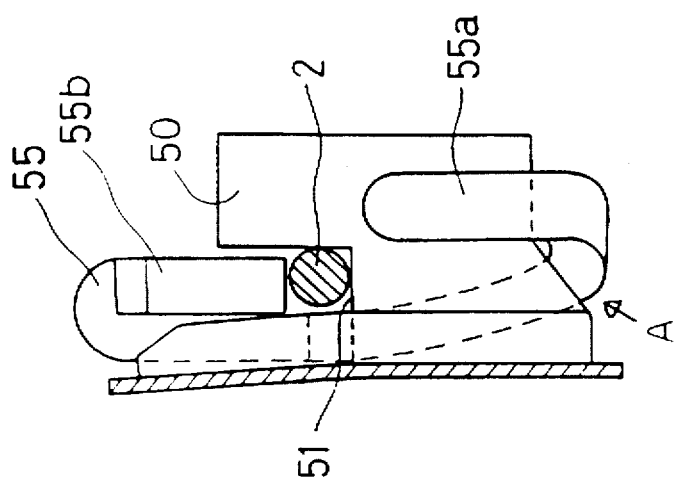
FIGS. 22(a) to 22(c) are views showing an orthodontic appliance of prior art (3).
Figure 22A:
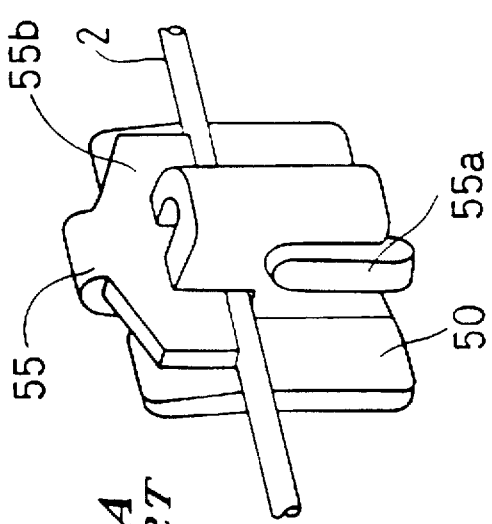
Figure 22C:
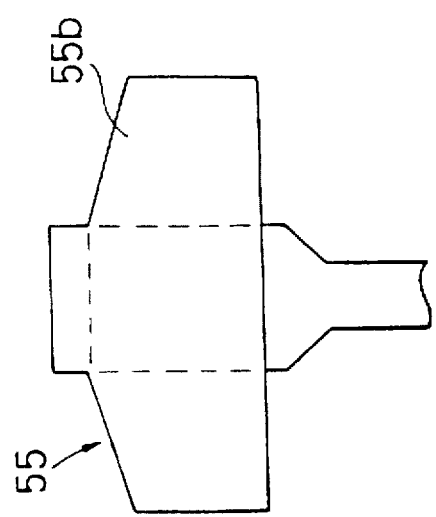

Likewise, in the orthodontic appliance of the prior art (3), because there occurs a gap in a portion A where the lower end 55a of the lock pin 55 is bent (see FIG. 22(b)), the lock pin cannot sufficiently hold the arch wire 2. This results in problems such as not applying the correct torque.

Figure 23A:
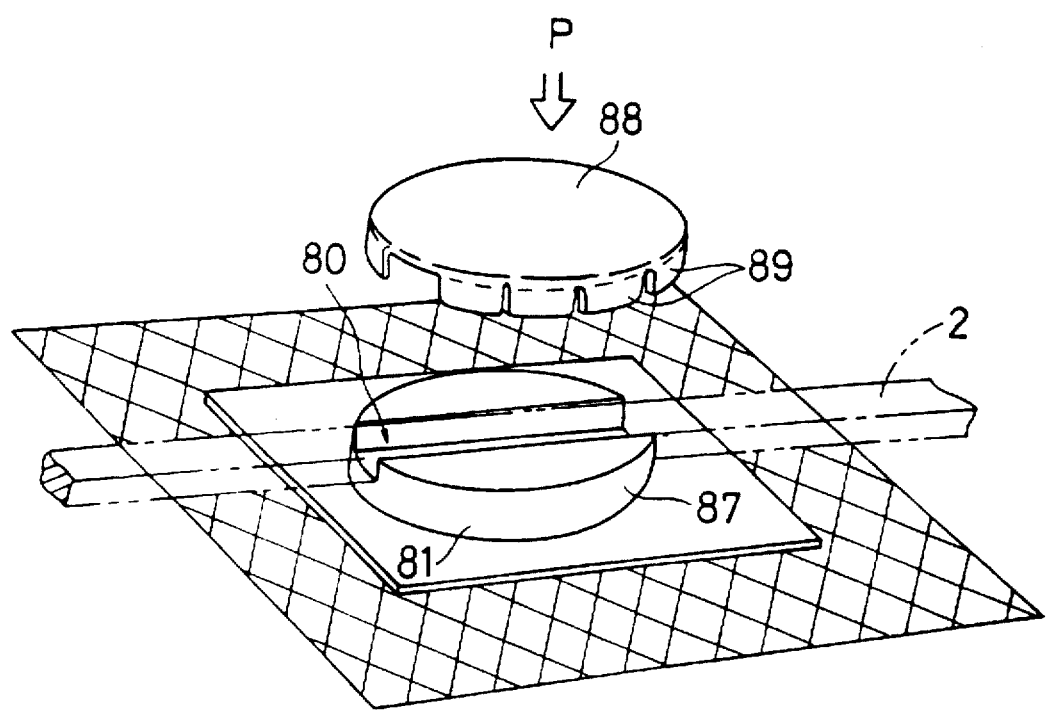
FIG. 23 is a perspective view of an orthodontic appliance of the prior art (4).

On the other hand, in prior art (4) (see FIG. 23), since the cover member 88 is removed by pressing the center thereof, a space is necessarily required between the arch wire 2 and an inner surface of the cover member 88. With the presence of a space, the arch wire 2 is floated and cannot be fixed tightly. If the arch wire 2 cannot be fixed tightly, the torque shift cannot be performed and the lateral movement of the arch wire 2 cannot be prevented.

The present invention has been made in view of the problems as set forth above and will be described below in conjunction with embodiments.

<First Embodiment>

Figure 1A:
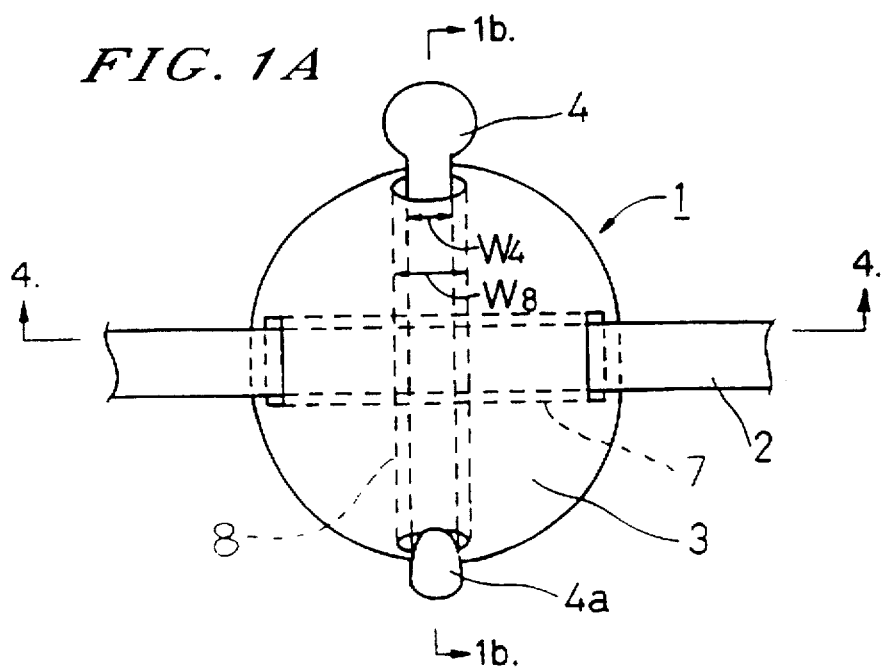
FIG. 1(a) is a front view of an arch wire and an orthodontic appliance according to a first embodiment of the present invention.
Figure 1B:
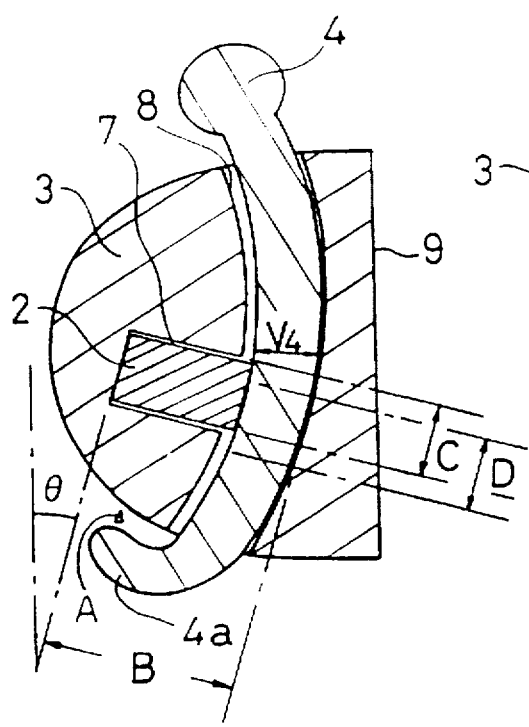
FIG. 1(b) is a sectional view taken along the line 1—1 in FIG. 1(a)
Figure 2:
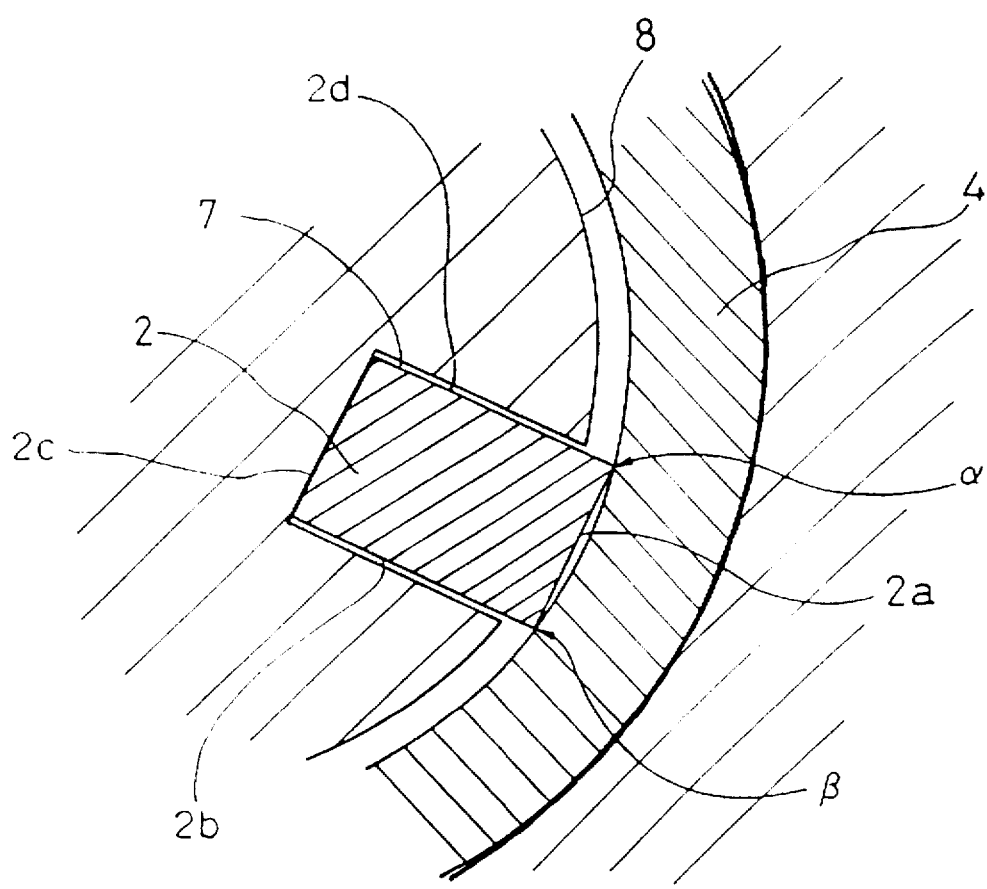
FIG. 2 is an enlarged sectional view of the arch wire and thereabout in FIG. 1(b).

FIG. 1(a) is a front view of an arch wire and an orthodontic appliance according to a first embodiment of the present invention, and FIG. 1(b) is a sectional view taken along the line 1b—1b in FIG. 1(a). FIG. 2 is an enlarged sectional view of the arch wire and thereabout in FIG. 1(b).

An orthodontic appliance 1 comprises a bracket 3 and a lock pin 4. The bracket 3 includes an arch wire passage 7 formed therein to extend substantially horizontally, and a lock pin insertion passage 8 formed therein to extend substantially vertically. The bracket 3 has an almost hemispherical shape having very small projections and recesses on its surface.

Figure 1C:
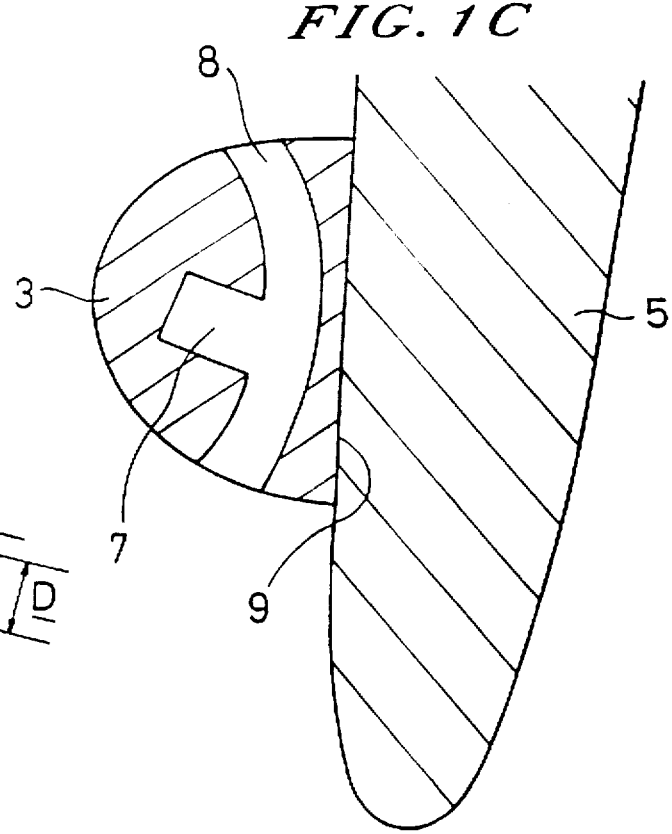
FIG. 1(c) is a sectional view showing a state where a bracket is bonded to a tooth.

FIG. 1(c) is a sectional view showing a state where the bracket 3 is bonded to a tooth 5. In treatment, as shown in FIG. 1(c), the bracket 3 is fixed to a front surface of the tooth 5 by an adhesive coated on a bonding surface 9 of the bracket.

In use of the orthodontic appliance 1, an arch wire 2 is inserted through the arch wire passage 7 and the lock pin 4 is inserted through the lock pin insertion passage 8.

The lock pin 4 is a bow-shaped bar jutting in its central portion toward the tooth surface. The lock pin insertion passage 8 also has a bow-shape having the same or a little smaller radius of the curvature as or than the lock pin 4 (i.e., having a sharper curve).

The lock pin insertion passage 8 is provided nearer to the tooth surface than the arch wire passage 7 so that, when the lock pin 4 is inserted through the lock pin insertion passage 8, the lock pin 4 presses the arch wire 2 toward the side farther from the tooth for positioning it. Specifically, a jutting surface of the bow-shaped lock pin 4 (i.e., a surface facing the tooth) is supported by an inner wall surface of the lock pin insertion passage 8, and an inner surface of the bow-shaped lock pin 4 presses the arch wire 2 toward the lip/cheek side. Then, the arch wire 2 is held at its lip/cheek side surface 2c against a groove wall surface of the arch wire passage 7 (see FIG.2). In this way, the arch wire 2 is tightly fixed to the orthodontic appliance 1 and, therefore, the force loaded on the arch wire 2 can correctly be transmitted to the orthodontic appliance 1.

A lower end portion 4a, in particular, a tip end of the lock pin 4 may be slightly tapered or diverted to a direction of slightly increasing the radius of curvature so that it is easily inserted through the lock pin insertion passage 8.

Figure 3:
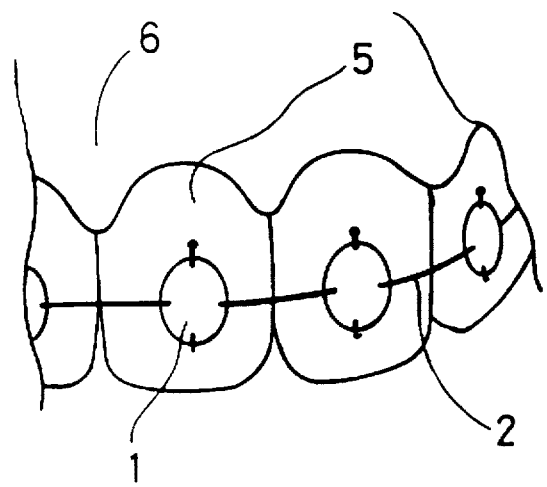
FIG. 3 is a front view of teeth, showing a state wherein the orthodontic appliances according to the first embodiment are used.

FIG. 3 is a front view of teeth, the view showing a state the orthodontic appliances 1 are used. The arch wire 2 is passed through the orthodontic appliances 1 fixed to the respective teeth 5 for straightening the line of teeth. Incidentally, denoted by 6 is the gum or teethridge.

In treatment, various degrees of strength of fixing the arch wire 2 from moderate to tight fixing are realized depending on the strength of fixing which is desired in each of the treatment stages, by selecting the thickness and shape of the arch wire 2 and the thickness of the lock pin 4. For example, if the total of the thickness of the arch wire 2 and the thickness $V_4$ of the lock pin 4 is sufficiently large with respect to the total width B (see FIG. 1(b)) of the arch wire passage 7 and the lock pin insertion passage 8 in an intersecting portion, the arch wire 2 can tightly fixed to the bracket 3. Conversely, if it is smaller, there occurs a play between the arch wire 2 and the bracket 3, thus providing moderate fixing.

In the past, the strength of fixing the arch wire 2 has been adjusted by increasing or reducing the strength of tightening the attachment wire in accordance with a perception of a dentist, and hence it has been determined depending on the skill of a dentist in many cases. By contrast, in this embodiment of the present invention, since the strength of fixing the arch wire 2 is automatically set by selecting the thickness of the arch wire 2 and the lock pin 4, the predetermined strength of fixing can be realized without depending on the skill of a dentist.

In the rough straightening stage of treatment, the arch wire 2 is moderately fixed to the bracket 3 by using the arch wire 2 which is round or square-shaped but relatively thin, or using the relatively thin lock pin 4. In some cases, the lock pin may be dispensed with. Additionally, it is advantageous that the lower end portion 4a of the lock pin 4 is bent in use to prevent the lock pin from slipping off naturally.

When the torque shift or the like is desired in the right position correcting stage, a square wire is employed as the arch wire 2. The arch wire 2 has a size corresponding to the arch wire passage 7 so that it can closely fitted to the arch wire passage 7 as shown in FIG. 1(b). The lock pin 4 is then inserted through the lock pin insertion passage 8 to fix the arch wire 2 while pressing it from the tooth side surface toward the lip/cheek side surface. At this time, the arch wire 2 and the lock pin 4 each having an appropriate thickness are selected so as to tightly fit the arch wire 2 without causing any play. After that, the lower end portion 4a of the lock pin is bent to prevent the lock pin from slipping off.

In each of prior art (2) and (3), the lock pin 4 is allowed to move vertically and hence cannot hold the arch wire tightly because of the gap occurred in the bent region of the lower end portion of the lock pin. In this first embodiment, however, even if the lock pin 4 is displaced vertically corresponding to the gap occurred in a bent region A of the lower end portion 4a, the lock pin 4 can continue pressing the arch wire 2 as explained below. Comparing the states before and after displacement of the lock pin 4, a portion C of the lock pin 4 (see FIG. 1(b)) which has pressed the arch wire 2 before the displacement is just shifted by a distance corresponding to the gap, and the arch wire 2 is pressed by another portion D of the lock pin 4 after the displacement. Because the portions C and D have the same thickness $V_4$, the force of pressing the arch wire 2 is not changed between the time period before and after the displacement of the lock pin 4. Accordingly, the fixing of the arch wire 2 will not be loosened and the torque shift can be correctly achieved corresponding to the torque angles θ.

It is impossible for the arch wire 2 and the arch wire passage 7 to have exactly the same size because the arch wire 2 must be inserted through the arch wire passage 7 in the treatment. Therefore, the arch wire 2 is necessarily set to be a little thinner. Thus-resulting gaps between the top surface 2d, the lip/cheek side surface 2c and the bottom surface 2b of the arch wire 2 and inner walls of the arch wire passage 7 (see FIGS. 1(b) and 2) may render the torque angle set to the arch wire passage 7 in the bracket 3 to be somewhat different from the torque angle actually applied to the arch wire 2. However, since the difference between the two torque angles is not unexpectable but can be calculated, the torque shift may be performed in consideration of the calculated angle.

Further, in the orthodontic appliance 1 of this first embodiment, tight fixing of the arch wire 2 is realized as described below in detail.

As will be seen from FIG. 2, since the lock pin 4 and the lock pin insertion passage 8 in this first embodiment are both bow-shaped, the arch wire 2 is pressed at two corners or edges of its tooth side surface 2a, i.e., at two points α and β shown in FIG. 2. If the lock pin 4 is a straight one, the arch wire 2 is pressed from the entire tooth side surface 2a. The pressing from the entire surface is identical to the pressing at one point. Thus, by pressing the arch wire 2 at two points as with this first embodiment, the arch wire 2 can be pressed more tightly.

Incidentally, since the lock pin 4 is tightly secured at the two points as explained above and will seldom slip off, it can be used without bending the lower end portion 4a in some cases.

A sectional shape of the lock pin 4 will now be described.

Through all the treatment stages, it is recommended that the transverse width (indicated by $W_4$ in FIG. 1(a)) of the lock pin 4 be slightly smaller than the transverse width (indicated by $W_B$ in FIG. 1(a)) of the lock pin insertion passage 8. This allows the lock pin 4 to abut ;it its left and right lateral surfaces against side walls of the lock pin insertion passage 8, thereby preventing the lock pin from wobbling laterally.

For the depthwise width or thickness (indicated by $V_4$ in FIG. 1(b)) of the lock pin 4, depending on the treatment stages, the lock pin having a relatively small thickness $V_4$ is used when moderate fixing is desired, and the lock pin having a relatively large thickness $V_4$ is used when tight fixing is desired, as explained above. In other words, the lock pin 4 is selected to have a cross-sectional shape of a thin ellipse being elongate in the direction of the transverse width $W_4$ when moderate fixing is desired. When desired tightness of the fixing is gradually increased, the lock pin 4 is selected to have a cross-sectional shape of an ellipse closer to a circle, a circle or an ellipse being elongate in the direction of the thickness $V_4$.

Further, when positive fixing is desired, it is recommended that the lock pin 4 and the lock pin insertion passage 8 be each polygonal in cross-section. If the lock pin 4 and the lock pin insertion passage 8 are each circular in cross-section, the lock pin 4 may rotate about the center of the circle. However if they each have a polygonal cross-section, the lock pin 4 will abut against inner walls of the lock pin insertion passage 8 and will not rotate even upon application of force tending to rotate the pin and, therefore, can stably be fixed without moving in the passage.

Figure 4:
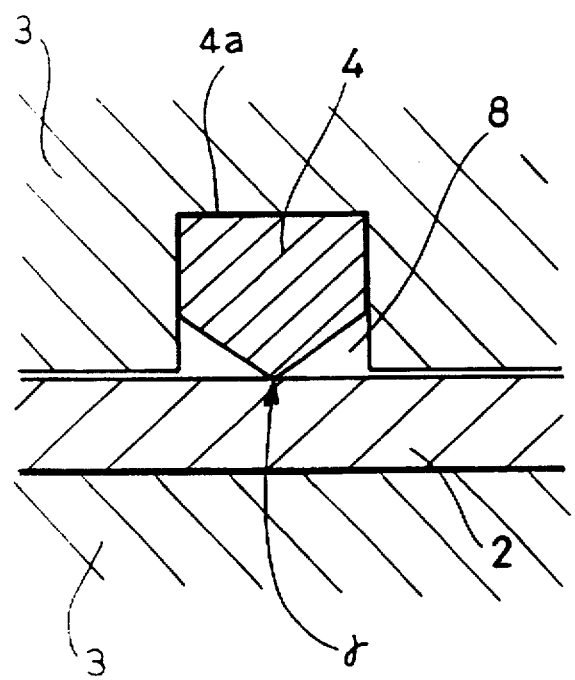
FIG. 4 is a sectional view showing one example of a lock pin and a lock pin insertion passage for use in the present invention.

FIG. 4 is a sectional view indicating cross-sectional shapes of the lock pin 4 and the lock pin insertion passage 8, the view showing a section of the lock pin 4 and its surrounding taken along the line 4—4 in FIG. 1(a).

The most recommended cross-section of the lock pin 4 is pentagonal (see FIG. 4). For the lock pin 4 being pentagonal in cross-section, a tooth side surface 4a of the lock pin 4 contacts a tooth side inner wall of the lock pin insertion passage 8, and an angled corner γ of the lock pin 4 in opposite relation to the tooth side surface 4a abuts against the arch wire 2. Thus, on the tooth side of the lock pin 4, the tooth side surface 4a and/or lateral surfaces on both sides thereof abut against inner walls of the lock pin insertion passage 8 which is rectangular in cross-section, thereby acting to prevent rotation of the lock pin 4. On the lip/cheek side (i.e., the arch wire side) of the lock pin 4, the angled corner γ serves to press the arch wire 2, meaning that the arch wire 2 can be fixed more tightly than the case of the lock pin 4 pressing the arch wire 2 in plane-to-plane contact.

Furthermore, the direction in which the lower end portion 4a of the lock pin 4 can be bent is determined so as to be any one of four directions when the cross-section of the lock pin 4 is square, and is limited to two directions along long sides when it is rectangular, which leads to inconvenience in treatment. When the cross-section of the lock pin 4 is pentagonal, the bending direction is not so limited and ensures better convenience. On the other hand, when the cross-section of the lock pin 4 is polygonal with a larger number of angles, such as heptagonal and octagonal, it approaches a circle, making it difficult to prevent the rotation of the lock pin 4. Consequently, the lock pin 4 having a pentagonal cross-section is most recommended.

As an alternative, the lock pin 4 having a semicircular cross-section is also preferred because a flat surface of the lock pin 4 abuts against the inner wall of the lock pin insertion passage 8 to prevent rotation of the lock pin 4 and an apex of the circular cross-section can press the arch wire 2 tightly, as with the pentagonal case.

<Second Embodiment>

A description will be made below of one example of recommended methods for fabricating the bracket in the first embodiment.

The bracket is manufactured firstly by fabricating a lip/cheek side member and a tooth surface side member of the bracket, and then joining these two members together.

FIG. 5 is a perspective view showing one example of each of the lip/cheek side member and the tooth surface side member of the bracket. Specifically, FIGS. 5(a) and 5(b) show joined surfaces of a tooth surface side member 10 and a lip/cheek side member 11, respectively. Note that the lip/cheek side member 11 and the tooth surface side member to are configured such that a completed bracket has the torque angle θ of 0 degree.

The lip/cheek side member 11 includes an arch wire accommodation groove 17 formed therein to extend substantially horizontally, and a lock pin insertion groove 18 formed therein to substantially vertically while curving in the shape of a bow. The lock pin insertion groove 18 is shallower than the arch wire accommodation groove 17. The tooth surface side member 10 includes a horizontal ridge 67 formed thereon to extend substantially horizontally in match with the arch wire accommodation groove 17, and a vertical ridge 68 formed thereon to extend substantially vertically to match with the lock pin insertion groove 18. The horizontal ridge 67 has such a projection height as not completely filling the arch wire accommodation groove 17, and the vertical ridge 68 is projected in a smaller height than the horizontal ridge 67.

The lip/cheek side member 11 and the tooth surface side member 10 are fitted and joined together under a pressing action to form a bracket having the same configuration as the bracket 3 shown in FIG. 1. When both the members are subjected to pressing, the horizontal ridge 67 is fitted to the arch wire accommodation groove 17 while pushing it to spread, and the vertical ridge 68 is fitted to the lock pin insertion groove 18 while pushing it to spread. As a result, the two members are joined together in such a manner that both the ridges 67, 68 are gripped respectively by the grooves 17, 18. In the joined state, a space defined by the arch wire accommodation groove 17 and the horizontal ridge 67 becomes the arch wire passage 7, whereas a space defined by the lock pin insertion groove 18 and the vertical ridge 68 becomes the lock pin insertion passage 8.

It is also conceivable to manufacture the hollow bracket by molding, but the method of molding the bracket would push up the cost and hence would be not suitable for mass production. By contrast, the above-explained method of joining the two members together under pressing is advantageous in reducing the cost.

Although the two members can alternatively be joined together by using an adhesive, this method accompanies a fear that the adhesive may possibly injure the human body. On the other hand, when the two members are joined together under pressing, there is no fear of injury caused by the adhesive because no adhesive is employed, and the completed bracket is more preferable as a component of the orthodontic appliance which is used in the mouth.

<Third and Fourth Embodiments>

When the arch wire is attached to the bracket in the treatment, it is required that the arch wire can be fitted to the brackets from the front of the patient at least for those brackets which are bonded to front teeth.

The following third and fourth embodiments are designed to cope with the problem of enabling the arch wire to be fitted to the brackets in a direction directly opposite to the patient.

Figure 6A:
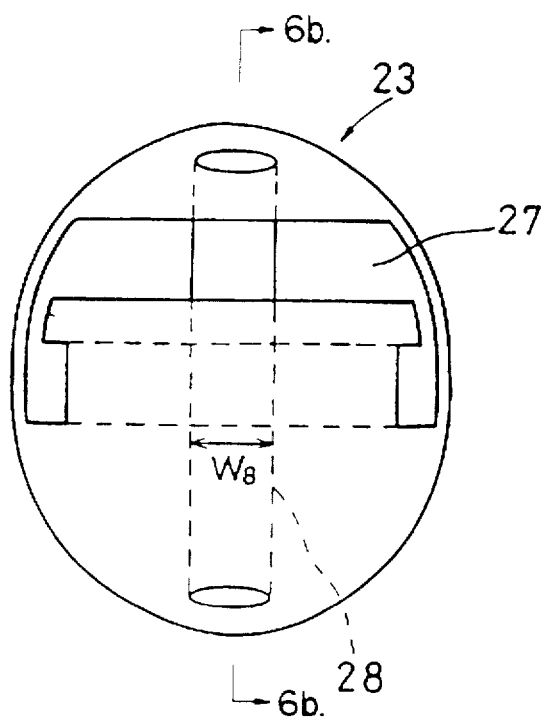
FIG. 6(a) is a front view of a bracket of an orthodontic appliance according to a third embodiment of the present invention.
Figure 6B:
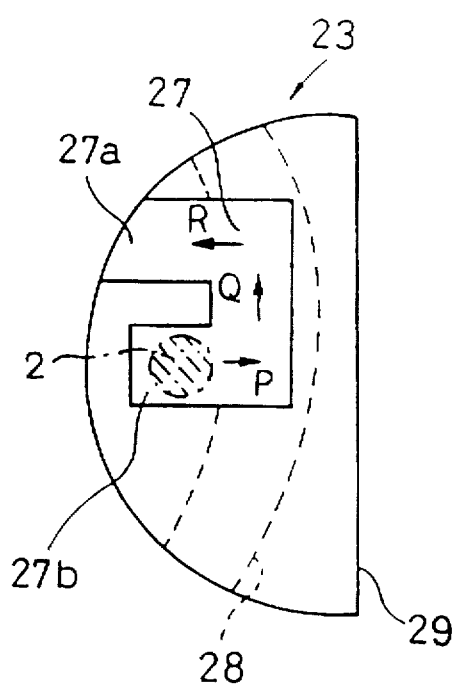
FIG. 6(b) is a right side view of the bracket, taken along line 6b—6b in FIG. 6(a)
Figure 6C:
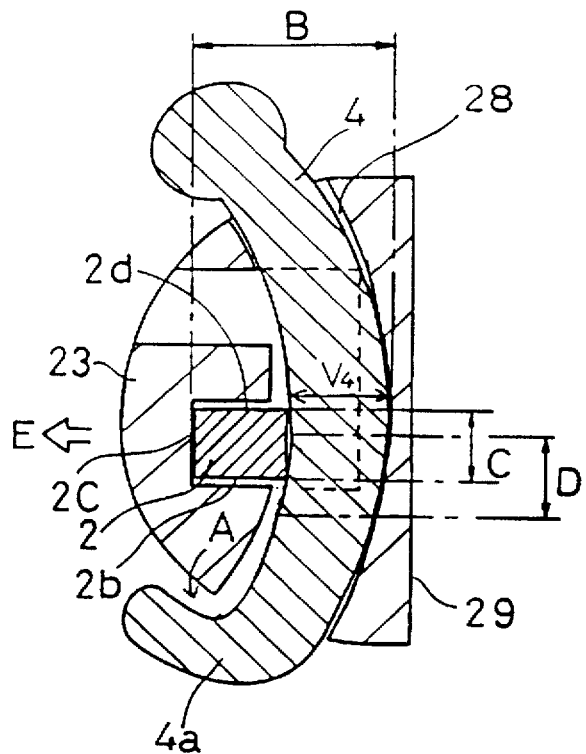
FIG. 6(c) is a sectional view of an arch wire and the orthodontic appliance according to the third embodiment.
Figure 7:
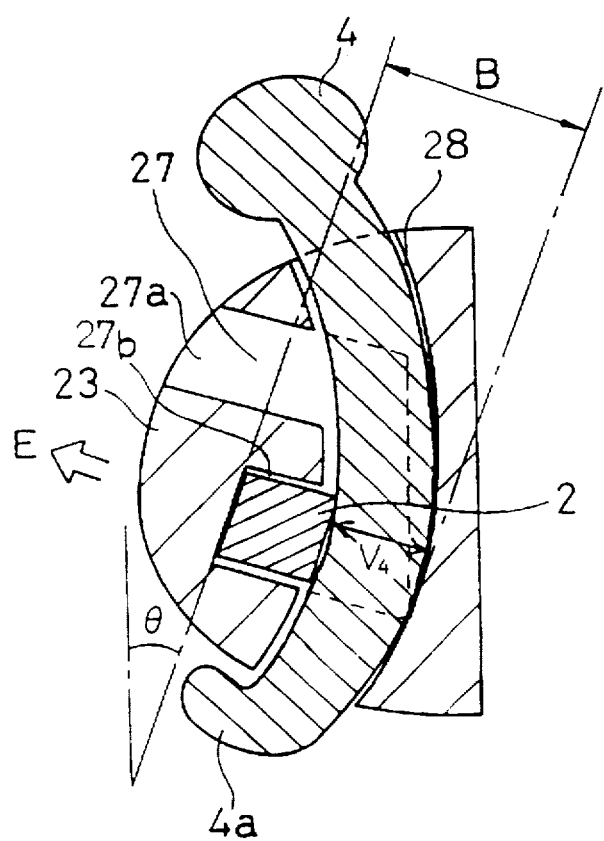
FIG. 7 is a sectional view of an arch wire and an orthodontic appliance according to a fourth embodiment of the present invention.

FIG. 6(a) is a front view of a bracket of an orthodontic appliance according to the third embodiment of the present invention, and FIG. 6(b) is a right side view of the bracket. FIG. 6(c) is a sectional view showing a state where an arch wire and a lock pin are inserted through the bracket, the view in FIG. 6b representing a section of the bracket taken along the line 6b—6b in FIG. 6(a). FIG. 7 is a sectional view of an arch wire and an orthodontic appliance (a bracket and a lock pin) according to the fourth embodiment of the present invention.

Each of orthodontic appliances according to the third and fourth embodiments comprises a bracket 23 and a lock pin 4. As will be seen from FIGS. 6 and 7, the bracket 23 includes an arch wire passage 27 formed therein to extend substantially horizontally. The arch wire passage 27 is in the form of a hooked groove which is bent at the bottom into a U-shape. A seated portion 27b is formed at the blind end of one part of the U-shaped groove extending toward the lip/cheek side, and an open portion 27a is formed at the open end of the other part of the U-shaped groove extending toward the lip/cheek side.

As with the above first embodiment, the lock pin 4 is bow-shaped and a lock pin insertion passage 28 also has a bow-shape having the same or a little smaller radius of the curvature as or than the lock pin 4. The lock pin insertion passage 28 is provided nearer to the tooth surface than the arch wire passage 27. Further, as with the above first embodiment, it is advantageous that a lower end portion 4a, in particular, a tip end of the lo(k pin 4 be slightly tapered so that it is easily inserted through the lock pin insertion passage 28.

While the seated portion 27b of the arch wire passage 27 has the torque angle θ in the third embodiment, it is formed to have the torque angle θ in the fourth embodiment.

In treatment, after coating an adhesive on a bonding surface 29, the bracket 23 is bonded to the tooth surface. An arch wire 2 is inserted to the arch wire passage 27 from the open portion 27a and then set in the seated portion 27b. Subsequently, the lock pin 4 is inserted through the lock pin insertion passage 28. Thus, in the third and fourth embodiments, the arch wire can be fitted in a direction directly opposite to the patient.

The arch wire 2 can be detached from the bracket 23 firstly by first moving it from the seated portion in a direction of arrow P, then lifting it in a direction of arrow Q, and withdrawing it in a direction of arrow R. In other words, the arch wire is dislodged only when movements of the arch wire in those three different directions are combined with one another in the above sequence. However since the arch wire inherently produces springback force acting in the direction of arrow R, it is prevented from moving in the direction of arrow P as the first step and will not be dislodged easily. Therefore, the arch wire will not slip off spontaneously before the lock pin is fitted in place, providing convenience in a treatment.

The arch wire 2 is fixed, as with the above first embodiment, by the lock pin 4 pressing the arch wire 2 in the seated portion 27b toward the lip/cheek side (i.e., in a direction of arrow E). More specifically, the lock pin 4 is supported at its tooth surface side surface by an inner wall of the lock pin insertion passage 28 and, simultaneously, presses the arch wire 2 toward the lip/cheek side. The arch wire 2 is held at its lip/cheek side surface 2c against a lip/cheek side surface of the seated portion 27b. In this way, the arch wire 2 is so tightly fixed to the orthodontic appliance that, as the arch wire 2 is moved, the orthodontic appliance is also moved together.

In treatment, as with the above first embodiment, various degrees of the strength of fixing the arch wire 2 from moderate to tight fixing are realized depending on the strength of fixing which is desired in each of the treatment stages, by selecting the thickness and shape of the arch wire 2 and the thickness of the lock pin 4. In the third and fourth embodiments, since the strength of fixing the arch wire 2 is automatically set by selecting the thickness of the arch wire 2 and the lock pin 4, the predetermined strength of fixing can be realized without depending on the skill of a dentist.

As described above, with the orthodontic appliances of the third and fourth embodiments, the arch wire can be fitted from the front of the teeth and held in place without using any additional attachment wire, and the instruments have the configuration having less projections and recesses on their surfaces. Therefore, dental plaque is difficult to become deposited on the instruments and, during tooth-brushing, a toothbrush can easily reach every corner of the instruments for easier cleaning. Further, since various degrees of the fixing strength from moderate to tight fixing can be realized by properly selecting the thickness and shape of the arch wire and the thickness of the lock pin, the orthodontic appliances of the present invention can be adapted for all the treatment stages from the rough straightening stage to the correct position correcting stage.

<Reference Example>

When tight fixing is not required through all stages of the treatment, the lock pin may be dispensed with as the following reference example.

Figure 8A:
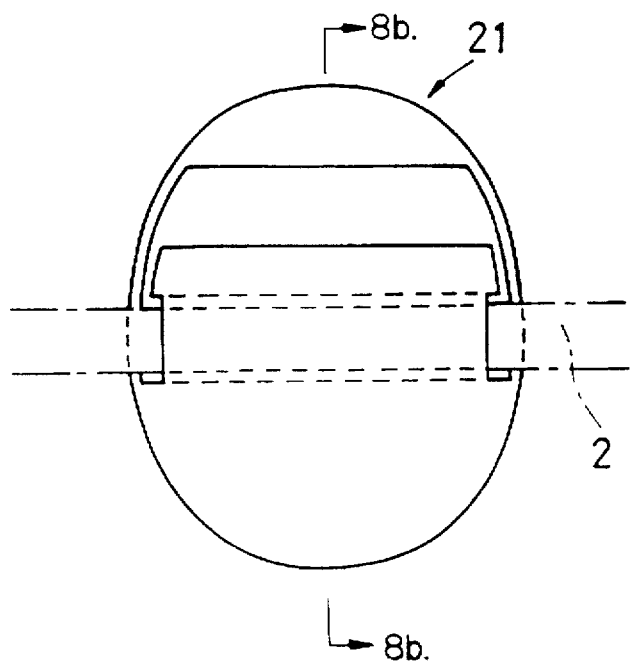
FIG. 8(a) is a front view of an orthodontic appliance according to a reference example.
Figure 8B:
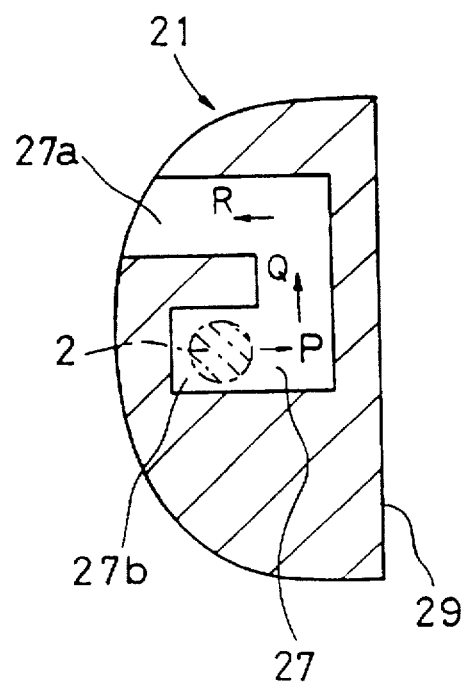
FIG. 8(b) is a sectional view taken along line 8b—8b in FIG. 8(a).
Figure 9A:
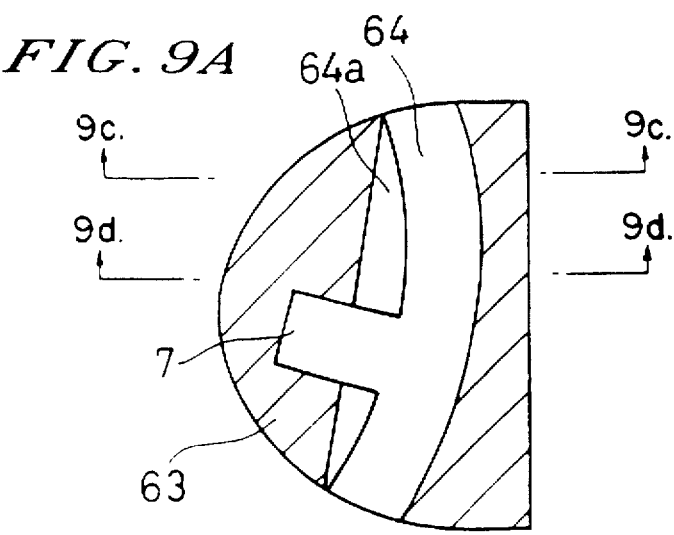
FIGS. 9(a) to 9(d) are views showing a bracket according to a fifth embodiment.
Figure 9B:
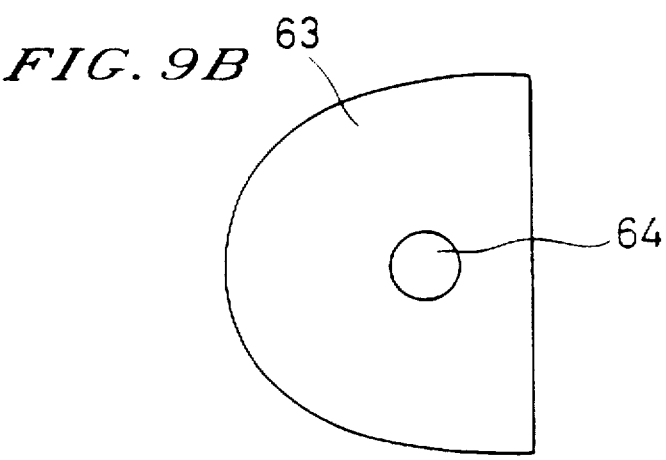
Figure 9C:
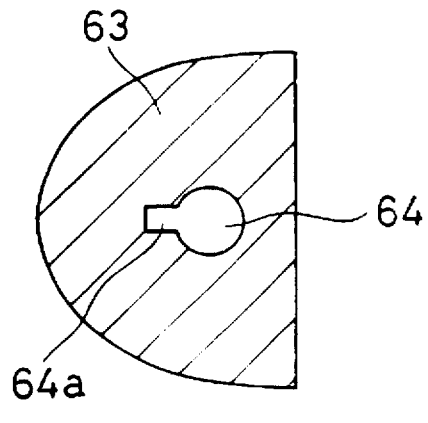
Figure 9D:
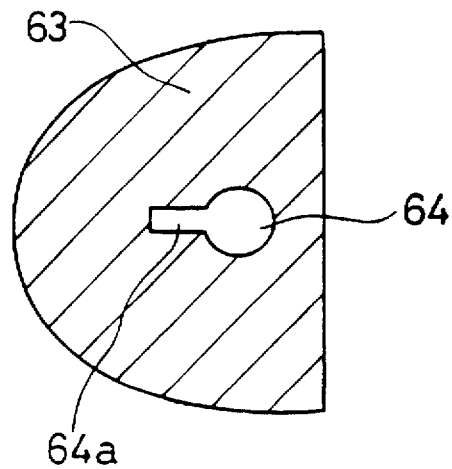

FIG. 8(a) is a front view of an orthodontic appliance according to the reference example, and FIG. 8(b) is a sectional view taken along the line 8b—8b in FIG. 8(a). As will be seen from FIG. 8, an orthodontic appliance 21 includes an arch wire passage 27 defined to extend substantially horizontally in the form of a hooked groove which is bent at the bottom into a U-shape. The arch wire passage 27 is opened as an open portion 27a at one end on the lip/cheek side, and has a seated portion 27b formed at the other blind end of the U-shaped groove toward the lip/cheek side.

<Fifth Embodiment>

A description will be made below of the case where it is desired to use a thin square arch wire 2 and achieve tight fixing in treatment.

Depending on treatment schedules, the treatment using a thin square arch wire 2 is desired in the right position correcting stage in rare cases. The arch wire 2 used in such a case is square in cross-section having a narrow width in the horizontal direction (corresponding to the direction indicated by B in FIG. 1(b)). When this arch wire 2 is fitted to the bracket 3 shown in FIG. 1 (first embodiment), the total thickness of the arch wire 2 and the thickness of the lock pin 4 is shorter than the width B, resulting in the problem that the arch wire 2 cannot be fixed tightly.

A bracket 63 shown in FIG. 9 represents a fifth embodiment designed to cope with the above-mentioned problem. FIG. 9(a) is a sectional view of the bracket 63 corresponding to the section taken along line 1b—1b in FIG. 1(a), FIG. 9(b) is a plan view of the bracket 63, FIG. 9(c) is a sectional view taken along the line 9c—9c in FIG. 9(a), and FIG. 9(d) is a sectional view taken along the line 9d—9d in FIG. 9(a). A lock pin insertion passage 64 includes a thin groove 64a formed in its inner wall on the lip/cheek side, and the thin groove 64a is defined so as to interconnect upper and lower ends of the arc of the bow-shaped lock pin insertion passage 64 by a straight line.

Figure 10:
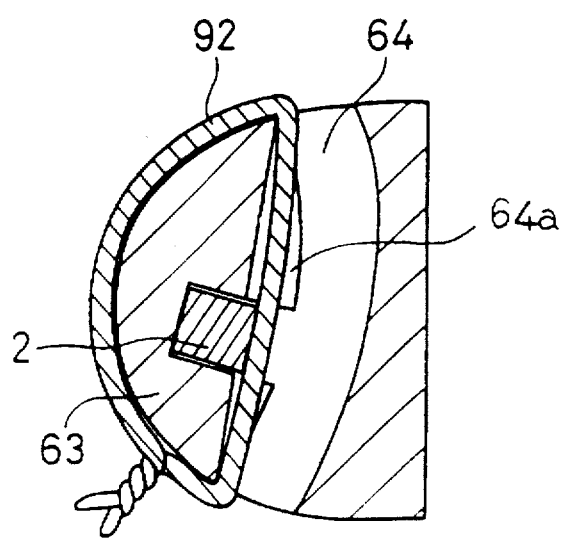
FIG. 10 is a sectional view showing a state where an arch wire is fixed to the bracket shown in FIG. 9.

When tight fixing is desired by using a thin square arch wire 2, an attachment wire 92 is inserted through the thin groove 64a of the lock pin insertion passage 64 and tied up as shown in FIG. 10. A portion of the attachment wire 92 which passes through the thin groove 64a abuts against the arch wire 2 so that the arch wire 2 can be fixed tightly.

When the attachment wire 92 is used for fixing the arch wire 2, projections and recesses on surfaces of the orthodontic appliance are increased and dental plaque is apt to be more easily deposited on the appliance. However, the fifth embodiment is intended to cope with a rare case in the treatment as mentioned above. Other than such a rare case, the tight fixing can be realized by using the orthodontic appliance which has the configuration having less projections and recesses on its surface and hence makes it hard for dental plaque to deposit thereon, and the bow-shaped lock pin to press the arch wire.

<Sixth Embodiment>

Another embodiment of the orthodontic appliance capable of fitting the arch wire from the front will be described below.

Figure 11A:
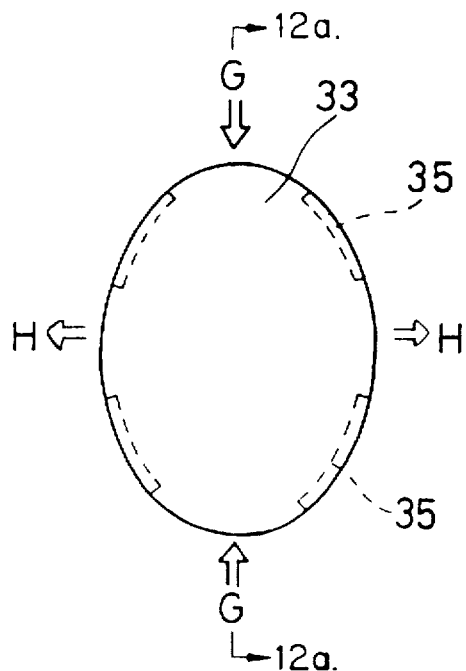
FIGS. 11(a) to 11(c) are front views of an orthodontic appliance (bracket) according to a sixth embodiment of the present invention.
Figure 11B:
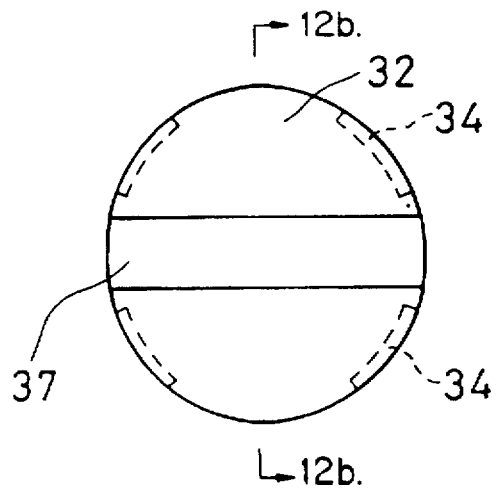
Figure 11C:
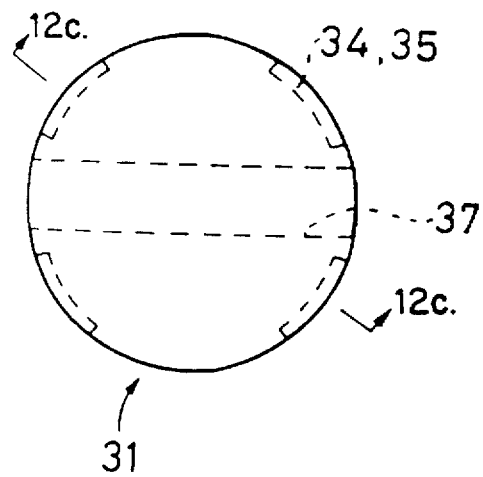
Figure 13A:
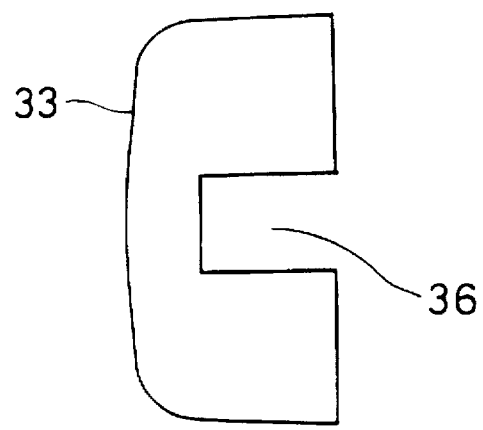
FIG. 13(a) is a side view of a bracket cover in the sixth embodiment.
Figure 13B:
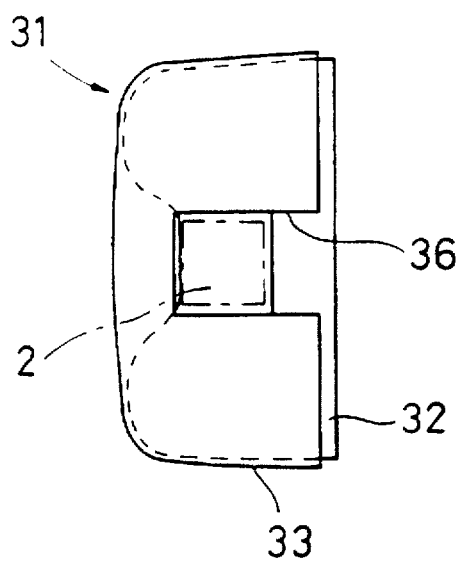
FIG. 13(b) is a side view of the bracket in the sixth embodiment

FIG. 11 is a front view of an orthodontic appliance (bracket) according to the sixth embodiment of the present invention, in which: FIG. 11(a) is a front view of a bracket cover 33, FIG. 11(b) is a front view of a bracket body 32, and FIG. 11(c) is a front view of a bracket 31 (completed by fitting the bracket cover 33 to the bracket body 32). FIG. 12(a) is a sectional view taken along the line 12a—12a in FIG. 11(a), FIG. 12(b) is a sectional view taken along the line 12b—12b in FIG. 11(b), and FIG. 12(c) is a sectional view taken along the line 12c—12c in FIG. 11(c). FIG. 13(a) is a side view of the bracket cover 33 [looking at FIG. 11(a) from the right or left], and FIG. 13(b) is a side view of the bracket 31 [looking at FIG. 11(c) from the right or left]. In FIG. 13(b), an arch wire 2 is indicated by one-dot-chain lines.

As will be seen from FIG. 11, the bracket body 32 has an elliptic shape being somewhat elongate in the vertical direction when viewed from the above, and the bracket cover 33 has the major axis longer than that of the bracket body 12 and the minor axis shorter than that of the bracket body 32. The bracket body 32 includes an arch wire insertion groove 37 formed in its middle portion to extend substantially horizontally, and engagement recesses 34 formed in its side or peripheral wall at upper and lower positions with the insertion groove 37 therebetween. Corresponding to the recesses 34, bosses 35 are formed in an inner side wall surface of the bracket cover 33 (see FIGS. 11 and 12). The bracket cover 33 is made of an elastic metal sheet and a cutout 36 corresponding to the arch wire insertion groove 37 is formed in each of opposite side surfaces of the bracket cover 33 (see FIG. 13). The bracket 31 (completed by fitting the bracket cover 33 to the bracket body 32) has a smooth surface having less projections and recesses.

A description will now be made of usage of the orthodontic appliance (bracket) according to the sixth embodiment and a mechanism for fixing the arch wire.

The bracket body 32 is bonded to the surface of a patient tooth by an adhesive coated on its bonding surface 32a.

For attaching the arch wire 2, the arch wire 2 is first accommodated in the arch wire insertion groove 37 of the bracket body 32. Then, the bracket cover 33 is pressed in directions of arrows G to slightly spread it in directions of the arrows H through elastic deformation to such an extent as it can loosely be fitted to the bracket body 32. Under such condition, the bracket cover 33 is fitted to the bracket body 32. Subsequently, by releasing the bracket cover 33 from the pressing in the directions of the arrows G, the bracket cover 33 is contracted in directions opposite to the directions of arrows If so as to restore its original shape, thereby sandwiching therebetween the bracket body 32 in the direction of width thereof. At this time, although the bracket cover 33 is slightly floated (separated) in directions opposite to the directions of the arrows G from the bracket body 32 due to its restoration, the bracket cover 33 can strongly grasp the bracket body 32 and can tightly be fixed in place by not only sandwich therebetween the bracket body 32 in directions opposite to the directions of the arrows H, but also engagement between the recesses 34 and the bosses 35.

The arch wire 2 is accommodated in a space (hereinafter referred to as an arch wire insertion space) defined by inner wall surfaces of the arch wire insertion groove 37 and the bracket cover 33. The arch wire insertion space is sized so as to just receive the arch wire 2 used in the right position correcting stage. Of four surfaces of the square arch wire 2, the lip/cheek side surface abuts against the inner wall surface of the bracket cover 33, whereas the other upper, tooth and lower side surfaces abut respectively against the inner wall surfaces of the arch wire insertion groove 37, thereby fixing the arch wire 2. In this way, the arch wire 2 is tightly fixed to the bracket 31 and, therefore, the force loaded on the arch wire 2 can correctly be transmitted to the bracket 31 for achieving the torque shift or the like.

In a treatment, as with the above first to fourth embodiments, the thickness and shape of the arch wire is selected depending on the strength of fixing the arch wire which is desired in each of the treatment stages, to adjust the play occurred between the arch wire insertion space and the arch wire for realizing various degrees of the fixing strength from moderate to tight fixing. In the rough straightening stage, for example, the arch wire 2 being round or having a thin square cross-section is selected for use so that the arch wire 2 is moderately fixed to the bracket 31. When the torque shift or the like is desired to be in the right position correcting stage, the arch wire 2 having a square cross-section sized to match with the arch wire insertion space so that the arch wire 2 is tightly fitted to the bracket 31.

When removing the bracket cover 33 as with the above fitting process, the bracket cover is pressed in the directions of arrows G to slightly spread it in the directions of the arrows 11 through elastic deformation to such an extent as it can be released from the bracket body 32 (see FIG. 11). At this time, the bosses 35 and the recesses 34 are also disengaged from each other upon deformation of the bracket cover 33, allowing removal of the bracket cover 33.

As described above, since the bracket of this sixth embodiment is arranged so as to attach and detach the bracket cover 33 by deforming its outer peripheral configuration, the bracket cover 33 can be attached and detached without needing any gap in the portion for accommodating the arch wire unlike prior art (4). It is therefore possible to replace the arch wire by different one and also tightly fix the arch wire.

The bracket body 32 and the bracket cover 33 are not limited to those configurations as shown in FIG. 11. For example, the bracket body 32 may have an elliptic shape in which the major axis is longer than that of the bracket cover and the minor axis is shorter than that of the bracket cover. Also, the elliptic shapes of the bracket body and the bracket cover are not limited to the illustrated ones being elongate in the vertical direction, but may be ones being elongate in the horizontal direction. Further, the elliptic bracket body and the elliptic bracket cover may be fitted to each other such that the minor axis of the bracket body aligns with the major axis of the bracket cover and the major axis of the bracket body aligns with the minor axis of the bracket cover. Additionally, a combination of the bracket body and the bracket cover may be modified such that one of them is circular and the other is elliptic.

In those modifications, the bracket cover is fitted to the bracket body by pressing the bracket cover in a direction of the axis (i.e., the major axis, minor axis or diameter) which is longer than the counterpart of the bracket body to slightly spread it in a direction of the axis which is shorter than the counterpart of the bracket body, and then releasing the bracket cover from the pressing. As a result, the bracket cover is fixed in place while sandwiching therebetween the bracket body due to its restoration.

<Seventh Embodiment>

An embodiment of the orthodontic appliance in which one of the bracket body and the bracket cover is circular and the other is elliptic, as suggested above, will be described below.

Figure 14A:
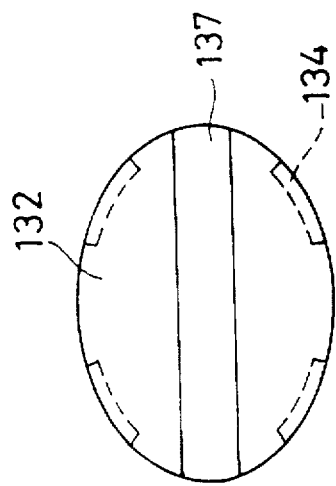
FIGS. 14(a) to 14(c) are front views of an orthodontic appliance (bracket) according to a seventh embodiment of the present invention.
Figure 14B:
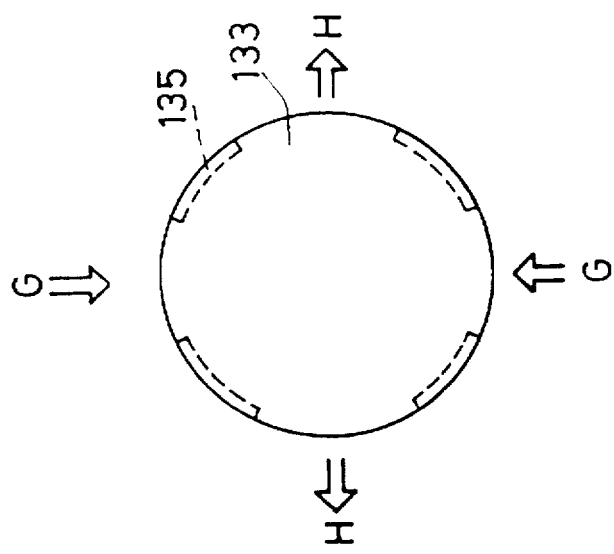
Figure 14C:
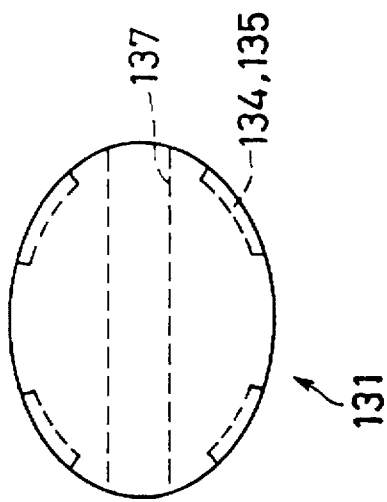

FIG. 14 is a front view of an orthodontic appliance (bracket) according to a seventh embodiment of the present invention, in which: FIG. 14(a) is a front view of a bracket cover 133, FIG. 14(b) is a front view of a bracket body 132, and FIG. 14(c) is a front view of a bracket 131 (completed by fitting the bracket cover to the bracket body).

The bracket body 132 has an elliptic shape being elongate in the horizontal direction when viewed from the above, and the bracket cover 133 is circular. The diameter of the bracket cover 133 is shorter than the major axis of the bracket body 32 and is longer than the minor axis thereof.

As with the above sixth embodiment, the bracket body 132 includes an arch wire insertion groove 137 formed in its middle portion to extend substantially horizontally, and engagement recesses 134 formed in its side or peripheral wall at upper and lower positions with the insertion groove 137 therebetween. Corresponding to the recesses 134, bosses 135 are formed in an inner side wall surface of the bracket cover 133. The bracket cover 133 is made of an elastic metal sheet and a cutout corresponding to the arch wire insertion groove 137 is formed in each of opposite side surfaces of the bracket cover 133. The bracket 131 (completed by fitting the bracket cover 133 to the bracket body 132) has a smooth surface having fewer projections and recesses.

Usage of the orthodontic appliance according to the seventh embodiment and a mechanism for fixing the arch wire are also similar to in the above sixth embodiment. More specifically, the arch wire 2 is firstly accommodated in the arch wire insertion groove 137 of the bracket body 132. Then, the bracket cover 133 is pressed in the directions of the arrows G to slightly spread it in directions of arrows H through elastic deformation to such an extent that it can loosely be fitted to the bracket body 132. Under such a condition, the bracket cover 133 is fitted to the bracket body 132. Subsequently, by releasing the bracket cover 133 from the pressing in the directions of arrows G, the bracket cover 133 is contracted in directions opposite to the directions of arrows 11 so as to restore its original shape, thereby sandwichingly grasping the bracket body 132 in the direction of width thereof. In this way, the bracket cover 133 is tightly fitted to the bracket body 132.

<Eighth Embodiment>

An embodiment of the orthodontic appliance which is of cover type like the above sixth and seventh embodiments and has a bow-shaped lock pin will be described below.

Figure 15A:
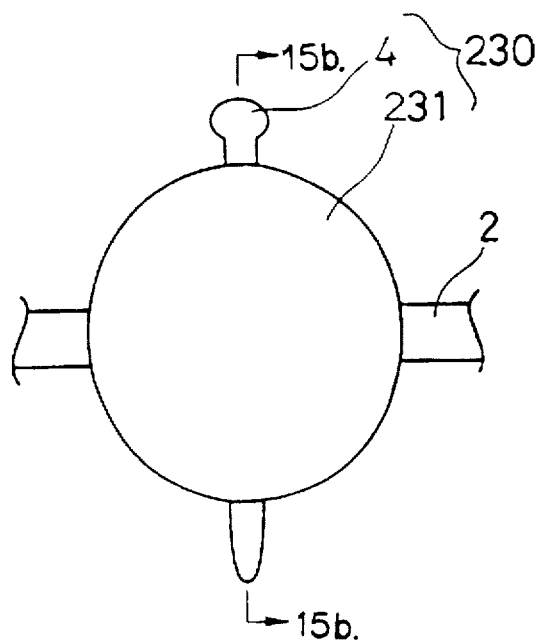
FIG. 15(a) is a front view of an arch wire and an orthodontic appliance according to an eighth embodiment of the present invention.
Figure 15B:
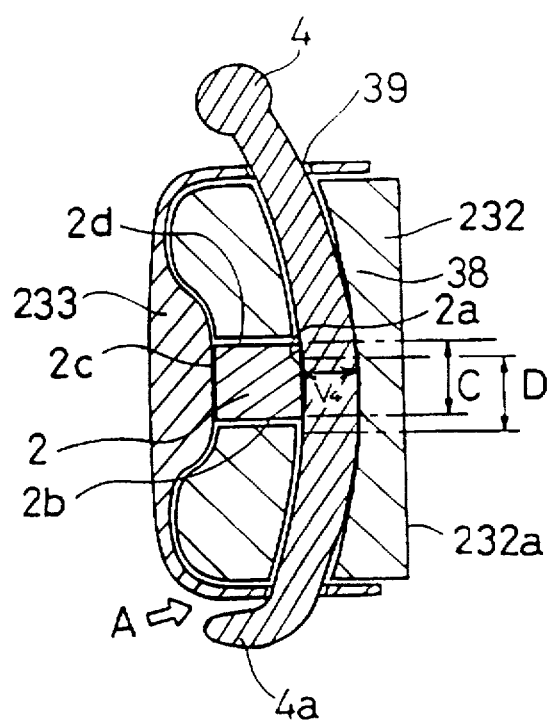
FIG. 15(b) is a sectional view taken along the line 15b—15b in FIG. 15(a)
Figure 15C:
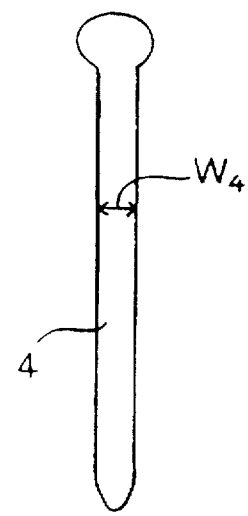
FIG. 15(c) is a front view of a lock pin.
Figure 16A:
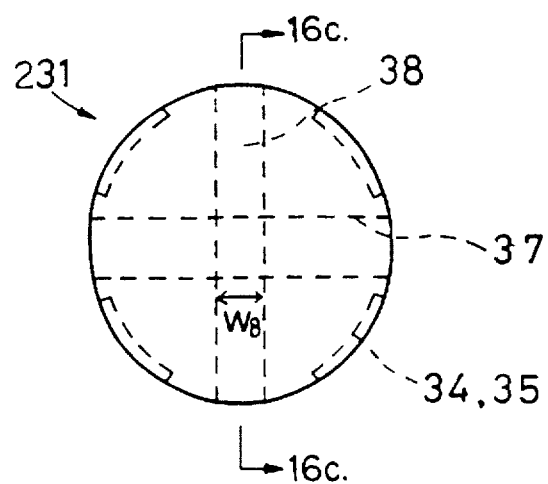
FIGS. 16(a) to 16(c) are views showing a bracket according to the eighth embodiment of the present invention.
Figure 16B:
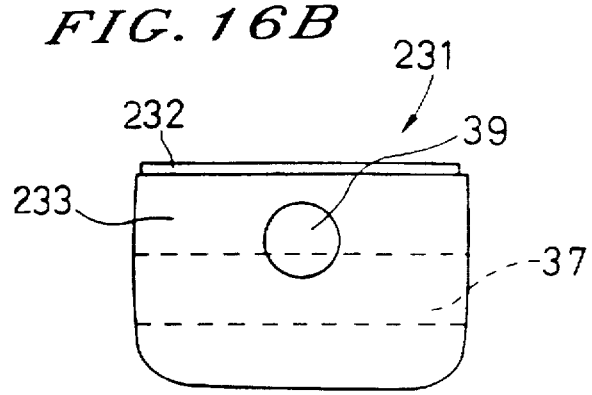
Figure 16C:
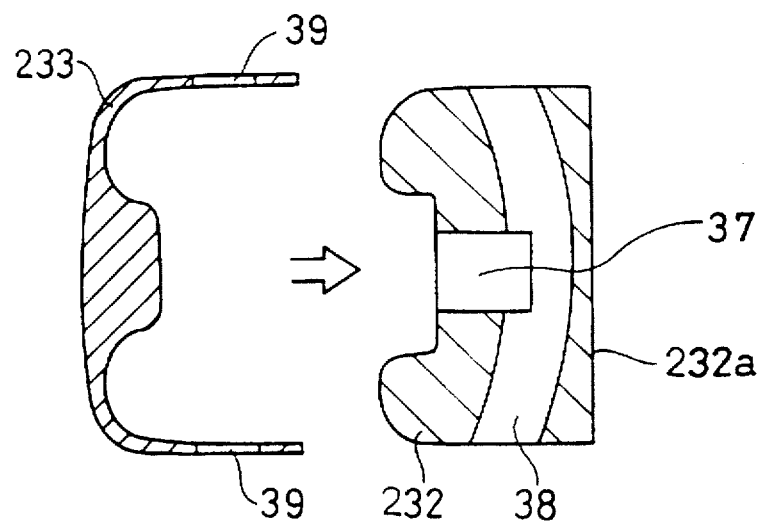

FIG. 15(a) is a front view showing a state where an arch wire 2 is inserted through an orthodontic appliance 230 comprising a lock pin 4 and a bracket 231, FIG. 15(b) is a sectional view taken along the line 15b—15b in FIG. 15(a), and FIG. 15(c) is a front view of the lock pin 4. FIG. 16 shows the bracket 231 in which: FIG. 16(a) is a front view, FIG. 16(b) is a plan view, and FIG. 16(c) is a sectional view taken along the line 16c—16c in FIG. 16(a), the view showing a state where a bracket body 232 and a bracket cover 233 are detached from each other. Note that the same components in FIGS. 15 and 16 as those in FIGS. 11 to 13 are denoted by the same reference numerals and will not be described below. In addition to the same arrangement as in the above sixth embodiment, the bracket body 232 and the bracket cover 233 are designed to have an additional arrangement below.

The bracket body 232 includes a lock pin insertion passage 38 formed therein to extend substantially perpendicularly to the arch wire insertion groove 37. The lock pin insertion passage 38 is provided nearer the tooth surface than the arch wire insertion groove 37, and has a bow-shape having the same or a little smaller radius of the curvature as or than the lock pin 4 which is also bow-shaped. The bracket cover 233 includes lock pin insertion holes 39 formed in match with the lock pin insertion passage 38. The lock pin 4 is the same as that used in the above first embodiment. In this eighth embodiment, it is also advantageous that a lower end portion 4a, in particular, a tip end of the lock pin 4 be slightly tapered so that it is easily inserted through the lock pin insertion passage 38.

Usage of the orthodontic appliance according to this eighth embodiment and the manner of fixing the arch wire 2 will be described below.

As with the above sixth embodiment, the bracket cover 33 is fitted to the bracket body 32 through which the arch wire 2 has been inserted, and the lock pin 4 is inserted through the lock pin insertion holes 39 and the lock pin insertion passage 38. It is advantageous that, after inserting the lock pin 4, its lower end portion 4a be bent to prevent the lock pin from slipping off spontaneously.

Upon the lock pin 4 being inserted through the lock pin insertion passage 38, the arch wire 2 inserted through the arch wire insertion groove 37 is pressed and fixed by the lock pin. At this time, the tooth side surface 2a of the arch wire 2 is pressed by the lock pin 4, the upper and lower surfaces 2d, 2b thereof are pressed by inner walls of the arch wire insertion groove 37, and the lip/cheek side surface 2c thereof is pressed by an inner surface of the bracket cover 33.

The upper and lower surfaces 2d, 2b of the arch wire 2 closely abut against the inner walls of the arch wire insertion groove 37 so as to cause no deviations, and the lip/cheek side surface 2c thereof also closely abut against the inner surface of the bracket cover 33 so as to cause no deviations. For another side (the tooth side surface 2a of the arch wire 2), even if the lock pin 4 is moved vertically to some extent, the pressing force exerted from an inner surface of the bow-shaped lock pin 4 remains the same as that explained in detail above in connection with the first embodiment and, therefore, the arch wire 2 will not be displaced. Such fixing of the arch wire is firmly realized by pressing it as follows. Specifically, a jutting surface of the bow-shaped lock pin 4 (i.e., a surface facing the tooth) is supported by an inner wall surface of the lock pin insertion passage 38, and the inner surface of the bow-shaped lock pin 4 presses the arch wire 2 toward the lip/cheek side. Then, the arch wire 2 is held at the lip/cheek side surface 2c against the inner surface of the bracket cover 233. In this way, the arch wire 2 is tightly fixed to the bracket cover 233. As the result, even if external forces are applied to the arch wire 2 under repeated chewing, the torque shift can be achieved as designed and the lateral movement of the arch wire can be prevented.

Further, in this eighth embodiment, since the bow-shaped lock pin is employed, the arch wire 2 can be fixed more tightly than the above sixth and seventh embodiments.

Figure 17:
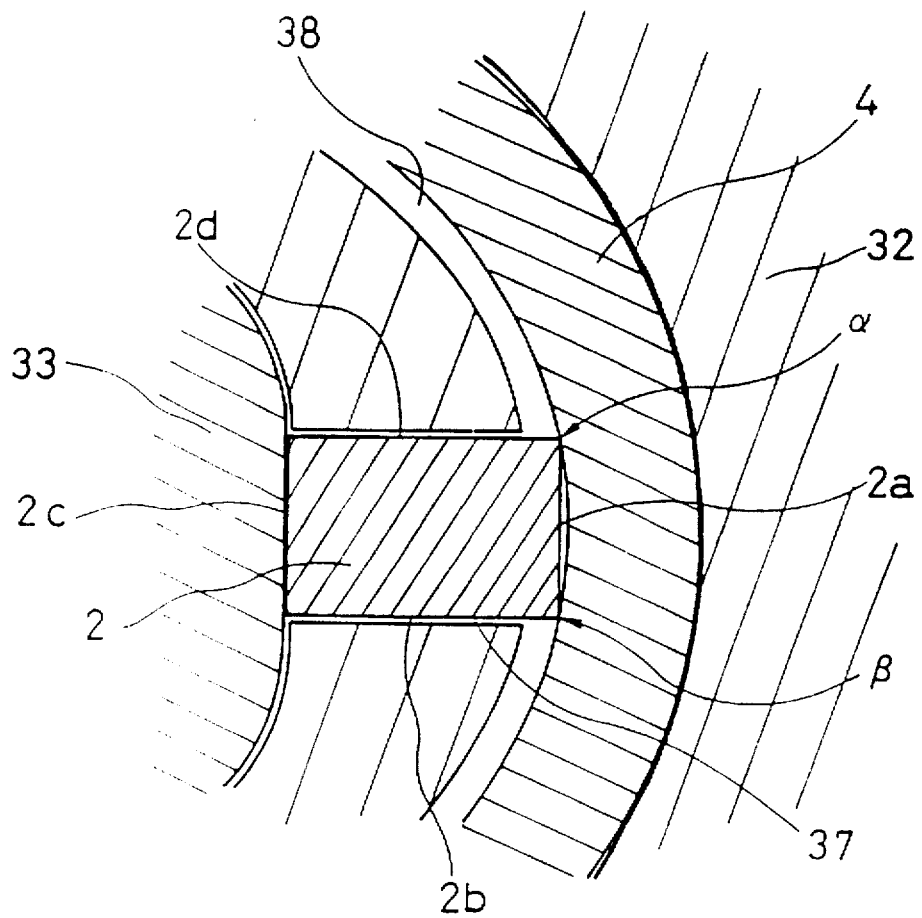
FIG. 17 is a sectional view of the arch wire and thereabout in FIG. 15(b).

FIG. 17 is an enlarged sectional view of the arch wire and thereabout in FIG. 15(b). In this eighth embodiment, since the lock pin 4 and the lock pin insertion passage 38 are both bow-shaped, the square arch wire 2 is also pressed at two corners or edges of its tooth side surface 2a, i.e., at two points α and β shown in FIG. 17, as with the above first embodiment. Therefore, the arch wire 2 can be fixed firmly.

Incidentally, since the lock pin 4 is tightly secured at the two points as explained above and will seldom slip off, it can be used without bending the lower end portion 4a in some cases.

As mentioned above, in match with the bow-shaped lock pin 4, the lock pin insertion passage 38 formed in the bracket body 232 has a bow-shape having the same or a little smaller radius of the curvature as or than the lock pin 4. If the lock pin insertion passage 38 is designed with a little smaller radius of the curvature than the lock pin 4, the tip end of the lock pin is guided by the bow-shaped wall surface of the lock pin insertion passage 38 on the outer or tooth side when the lock pin is inserted. Accordingly, the tip end of the lock pin will not be caught by the corner of the arch wire 2 and hence the lock pin will not suffer from any blockage during its insertion, allowing the dentist to smoothly perform the treatment.

In a treatment, as with the above first embodiment and so on, various degrees of strength of fixing the arch wire 2 from moderate to tight fixing are realized by properly selecting the thickness and shape of the arch wire 2 and the thickness of the lock pin 4. For example, if the total of the thickness of the arch wire 2 and the thickness of the lock pin 4 is sufficiently large with respect to the arch wire insertion space, the arch wire 2 can tightly fixed to the bracket 3. Conversely, if it is smaller, there occurs a play between the arch wire 2 and the bracket 3, providing moderate fixing.

In the past, the strength of fixing the arch wire 2 has been adjusted by increasing or reducing the strength of tightening the attachment wire in accordance with a perception of a dentist, and hence it has been determined depending on the skill of a dentist in many cases. By contrast, in this eighth embodiment, since the strength of fixing the arch wire 2 is automatically set by selecting the thickness of the arch wire 2 and the lock pin 4, the predetermined strength of fixing can also be realized without depending on the skill of a dentist as with the above first embodiment and so on.

The lock pin 4 is locked in place by bending its lower end portion 4a, but some gap is inevitably caused along a bent region (see a portion indicated by arrow A in FIG. 15(b)).

Even if the lock pin 4 is displaced vertically corresponding to the gap occurred, the lock pin 4 can continue pressing the arch wire 2 as explained before. More specifically, a portion C of the lock pin 4 (see FIG. 15(b)) which has pressed the arch wire 2 before the displacement is just shifted by a distance corresponding to the gap, and the arch wire 2 is pressed by a portion D of the lock pin 4 after the displacement. Because the thickness of portions C and D is not changed, the force of pressing the arch wire 2 is not changed between before and after the displacement of the lock pin 4. Accordingly, the fixing of the arch wire 2 will not be loosened and the torque shift or the like can be achieved correctly.

The lock pin 4 and the lock pin insertion passage 38 are designed as fully described above in connection with the first embodiment.

<Ninth Embodiment>

Figure 18:
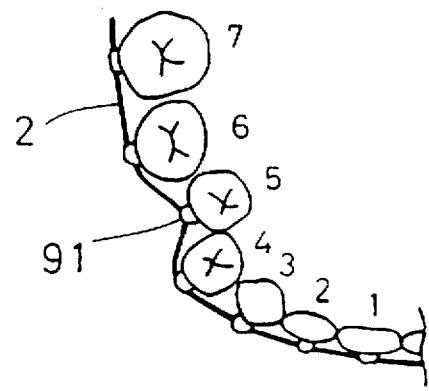
FIG. 18 is a view for explaining how to use orthodontic appliances according to a ninth embodiment of the present invention, the view showing teeth on the lower right jaw.

For example, supposing that one of teeth is positioned extremely inwardly from the normal line of the teeth like the 5th premolar tooth as shown in FIG. 18, if any of the orthodontic appliances according to the first, second, and fifth to eighth embodiments is employed, there arises a trouble that the arch wire 2 cannot be inserted through the arch wire passage. More specifically, the arch wire 2 is inserted through the arch wire passages of the respective brackets from the front of the patient's face in the sequence of a dog tooth, 4th premolar tooth, 5th premolar tooth, 6th molar tooth, and 7th molar tooth. However when the arch wire 2 is inserted through the bracket 3 bonded to the 5th premolar tooth, this inserting operation is difficult to carry out because the arch wire 2 led out of the 4th premolar tooth must be inserted with bending it extremely. Also, even if the arch wire 2 can be inserted through the bracket bonded to the 5th premolar tooth, the arch wire 2 must be then inserted through the bracket bonded to the 6th molar tooth with bending it extremely outwardly from the 5th premolar tooth. This inserting operation is also very difficult to carry out. Incidentally, that problem is not raised for the orthodontic appliances according to the third and fourth embodiments of the type capable of fitting the arch wire 2 from the front of the teeth.

Figure 19A:
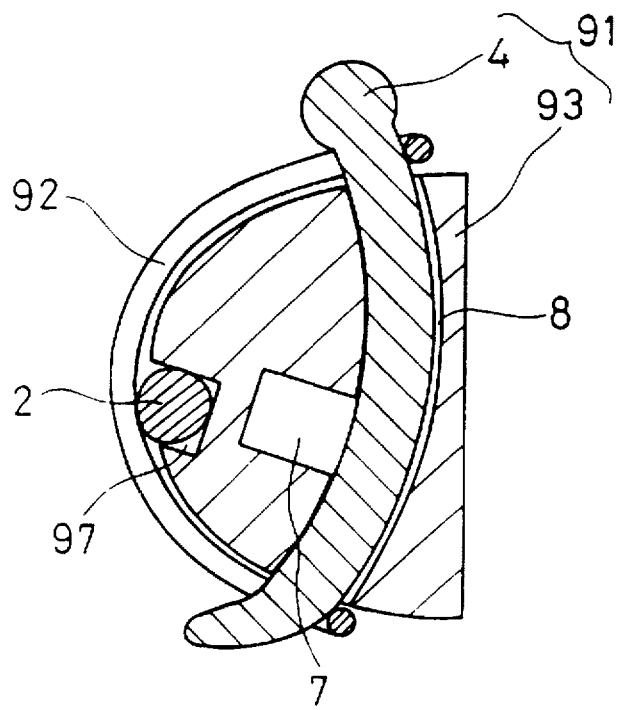
FIGS. 19(a) and 19(b) are sectional views of an attachment wire, an arch wire and the orthodontic appliance according to the ninth embodiment of the present invention.
Figure 19B:
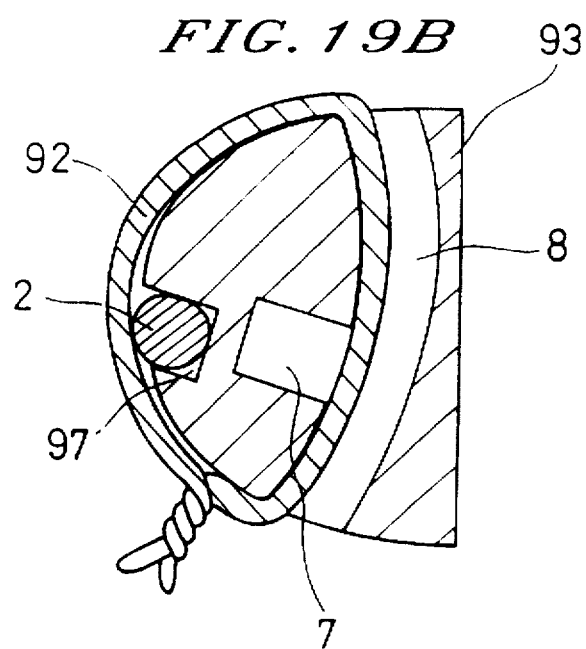
Figure 20A:
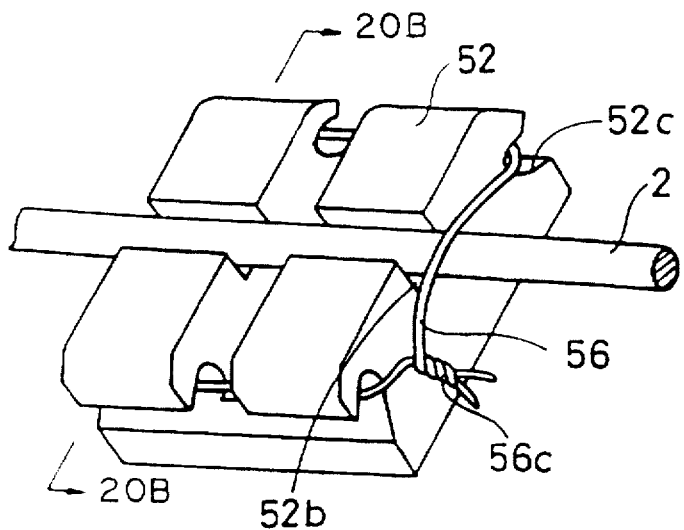
FIGS. 20(a) to 20(c) are views showing an orthodontic appliance of prior art (1).
Figure 20B:
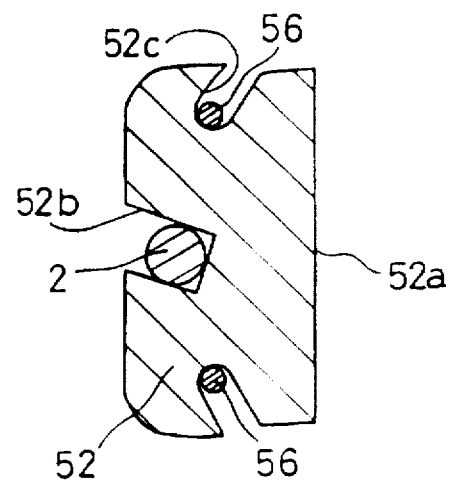
Figure 20C:
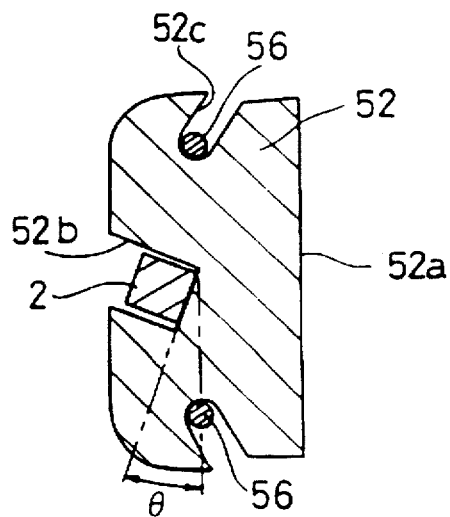

This ninth embodiment is intended to solve the above problem by modifying the orthodontic appliance of the first embodiment, and provides an orthodontic appliance adapted for a tooth which is positioned extremely inwardly as with the 5th premolar tooth illustrated above. FIG. 19(a) is a sectional view of an orthodontic appliance 91 (a bracket 93 and a lock pin 4) according to this ninth embodiment, the view showing a state where an arch wire 2 is fitted to the orthodontic appliance 91 and then fixed in place by an attachment wire 92. FIG. 19(b) is a sectional view showing a state where the arch wire 2 is fixed by the attachment wire 92 without using the lock pin 4.

The orthodontic appliance 91 comprises the bracket 93 and the lock pin 4. The bracket 93 includes an arch wire insertion groove 97 formed in its lip/cheek side surface to extend substantially horizontally. The depth of the arch wire insertion groove 97 is required to be not smaller than a half the thickness of the arch wire 2. As with the bracket 3 in the above first embodiment, an arch wire passage 7 extending substantially horizontally and a lock pin insertion passage 8 extending substantially vertically are formed in the bracket 93.

FIG. 18 shows a state where the orthodontic appliance 91 according to this ninth embodiment is used. As shown in FIG. 18, the orthodontic appliance 91 is employed for a teeth which is positioned extremely inwardly. It is preferably that the orthodontic appliance according to the above first embodiment be used for the other teeth.

In an initial stage of a treatment, when the relevant tooth is positioned extremely inwardly from the normal line of the teeth, the arch wire 2 is fitted to the arch wire insertion groove 97 and the attachment wire 92 is then tied up with passing it around the lock pin 4, thereby fixing the arch wire 2, as shown in FIG. 19(a). Alternatively, as shown in FIG. 19(b), the attachment wire 92 is inserted through the lock pin insertion passage 8 and then tied up so that the arch wire 2 fitted to the arch wire insertion groove 97 is fixed by the attachment wire 92.

After that, when the line of the teeth is straightened to such an extent as the arch wire 2 can be inserted through the arch wire passage 7, the arch wire 2 is inserted through the arch wire passage 7 and then fixed by the lock pin 4, as with the above first embodiment, for further straightening of the line of teeth. In this treatment stage, the attachment wire 92 is no longer required.

As described above, according to this ninth embodiment, even when one tooth is so obliquely grown as to make it difficult to insert the arch wire 2 through the arch wire passage 7, the arch wire 2 can be fitted to the orthodontic appliance 91 bonded to that tooth.

While projections and recesses are somewhat increased in the treatment stage using the attachment wire 92, projections and recesses are reduced and dental plaque becomes less liable to deposit on the appliance in the treatment stage not using the attachment wire 92.

The orthodontic appliances according to the first to ninth embodiments may be used for orthodontics in such a combined manner that any of those instruments of the type capable or fitting the arch wire from the front of the patient is bonded to a front tooth and/or a dog tooth, and any of those instruments of the type not capable of fitting the arch wire from the front of the patient is bonded to each of the other teeth.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims and therefore intended to be embraced therein.

We claim:

1. An orthodontic appliance comprising:
  a bracket having an arch wire passage formed therein to extend substantially horizontally and a lock pin insertion passage for insertion of a lock pin therethrough, and the lock pin being insertable through said bracket substantially vertically between the surface of a tooth and said arch wire passage for pressing an arch wire toward a side farther from a surface of the tooth to thereby position the arch wire, wherein:
  said lock pin insertion passage has a bow-shape jutable toward the tooth surface, and said lock pin is bow-shaped and the following mathematical expression is satisfied:

$$R_P \leq R_L$$

wherein $R_P$ is a radius of curvature for said lock pin insertion passage; and $R_L$ is a radius of curvature for said lock pin;

such that the inner surface of the bow-shaped portion of said lock pin presses said arch wire.

2. An orthodontic appliance according to claim 1, wherein said arch wire passage is in the form of a hooked groove with one end on the lip/cheek side left open, said groove being bent at a bottom portion thereof so as to be U-shaped in vertical section and extended back toward a side thereof not having an opening formed therein so as to form an arch wire seated portion.

3. An orthodontic appliance according to claim 1, wherein said bracket comprises first and second side members which are undetachably joined together.

4. An orthodontic appliance according to claim 3, wherein said first side member includes an arch wire accommodation groove extending substantially horizontally, and a lock pin insertion groove which is shallower than said arch wire accommodation groove and extends vertically while curving in a bow-shape, said second member includes a horizontal ridge extending substantially horizontally so as to match with said arch wire accommodation groove and having such a projection height so as not to completely fill said arch wire accommodation groove, and a vertical ridge extending substantially vertically so as to match with said lock pin insertion groove and projecting with a smaller height than said horizontal ridge, and said first and second members are fitted to each other under a pressing action into a unitary structure.

5. An orthodontic appliance according to claim 1, wherein the mathematical symbol $R_P$ is a radius of curvature for the inner surface of said lock pin insertion passage on a first side away from the tooth; and the mathematical symbol $R_L$ is a radius of curvature for the inner surface of bow-shaped lock pin.

6. An orthodontic appliance wherein a bracket having an arch wire passage comprising a bracket body fixable to a surface of a tooth and a bracket cover covering said bracket body in a detachable manner, wherein said bracket cover comprises an elastic material, said bracket cover and said bracket body are both elliptical shaped as viewed from the front side, one of the major axis and the minor axis of said elliptical bracket cover is longer than one of the major axis and the minor axis of said bracket body, and the other of the major axis and the minor axis of said bracket cover is shorter than the other of the major axis and the minor axis of said bracket body.

7. An orthodontic appliance according to claim 6, which comprises a bracket and a lock pin for positioning an arch wire in said bracket, wherein said bracket is formed with both an arch wire insertion passage and a lock pin insertion passage therein, said lock pin insertion passage is bow shaped jutting towards a tooth side thereof, said lock pin is bow shaped, and the following mathematical expression is satisfied:

$$R_P \leq R_L$$

where $R_P$ is a radius of curvature for said lock pin insertion passage and, $R_L$ is a radius of curvature for said lock pin such that the inner surface of the bow-shaped portion of said lock pin presses said arch wire.

8. An orthodontic appliance comprising a bracket body fixed to the surface of a tooth and a bracket cover covering said bracket body in a detachable manner, wherein:

said bracket cover comprises an elastic material, one of said cover and said bracket body is circularly shaped and the other is elliptically shaped, and the major axis of the elliptic shape is longer than the diameter of the circular shape and the diameter of the circular shape is longer than the minor axis of said elliptic shape.

9. An orthodontic appliance according to claim 8, which comprises a bracket and a lock pin positioning an arch wire in said bracket, wherein said bracket has both an arch wire insertion passage and a lock pin insertion passage formed therein, said lock pin insertion passage is bow shaped jutting towards a tooth side thereof, said lock pin is in bow shaped, and the following mathematical expression is satisfied:

$$R_P \leq R_L$$

where $R_P$ is a radius of curvature for said lock pin insertion passage and, $R_L$ is a radius of curvature for said lock pin such that the inner surface of the bow-shaped portion of said lock pin presses said arch wire.

10. An orthodontic appliance according to claim 8, wherein said bracket cover is elliptically shaped and said bracket body is circularly shaped.

11. An orthodontic appliance according to claim 8, wherein said bracket body is elliptically shaped and said bracket cover is circularly shaped.

* * * * *